(12) United States Patent
Bauer-Espindola et al.

(10) Patent No.: US 11,774,395 B2
(45) Date of Patent: *Oct. 3, 2023

(54) TEST ELEMENT FOR ELECTROCHEMICALLY DETECTING AT LEAST ONE ANALYTE

(71) Applicant: Roche Diagnostics Operations, Inc., Indianapolis, IN (US)

(72) Inventors: Klaus Andreas Bauer-Espindola, Mannheim (DE); Michael Marquant, Mannheim (DE); Christine Nortmeyer, Mannheim (DE); Reiner Stein, Bad Kreuznach (DE)

(73) Assignee: Roche Diagnostics Operations, Inc, Indianapolis, IN (US)

( * ) Notice: Subject to any disclaimer, the term of this patent is extended or adjusted under 35 U.S.C. 154(b) by 132 days.

This patent is subject to a terminal disclaimer.

(21) Appl. No.: 17/106,620

(22) Filed: Nov. 30, 2020

(65) Prior Publication Data

US 2021/0080420 A1    Mar. 18, 2021

Related U.S. Application Data

(63) Continuation of application No. 15/604,017, filed on May 24, 2017, now Pat. No. 11,099,149, which is a
(Continued)

(30) Foreign Application Priority Data

Dec. 19, 2014   (EP) ..................... 14199341

(51) Int. Cl.
*G01N 27/327* (2006.01)
*C12Q 1/00* (2006.01)

(52) U.S. Cl.
CPC ......... *G01N 27/3272* (2013.01); *C12Q 1/006* (2013.01); *G01N 27/3274* (2013.01)

(58) Field of Classification Search
None
See application file for complete search history.

(56) References Cited

U.S. PATENT DOCUMENTS 5,437,999 A    8/1995   Diebold et al.
RE44,521 E    10/2013   Musho et al.
(Continued)

FOREIGN PATENT DOCUMENTS

EP    0964059 A2    12/1999
EP    1253204 A2    10/2002
(Continued)

OTHER PUBLICATIONS

Heller, Adam and Feldman, Ben, Electrochemistry in Diabetes Management, Accounts of Chemical Research, 2010, pp. 963-973, vol. 43, No. 7.
(Continued)

*Primary Examiner* — J. Christopher Ball
(74) *Attorney, Agent, or Firm* — Roche Diagnostics Operations, Inc.

(57) ABSTRACT

A test element for electrochemically detecting at least one analyte in a bodily fluid is disclosed. The test element comprises at least one first electrode and at least one second electrode. The first electrode is designed as a working electrode and the second electrode is designed as a counter electrode. The test element comprises at least one capillary capable of receiving a sample of the body fluid. The first electrode and the second electrode are arranged on opposing sides of the capillary. The first electrode and the second
(Continued)

electrode are arranged such that during a capillary filling the first electrode and the second electrode are wetted simultaneously and at an equal rate.

12 Claims, 14 Drawing Sheets

Related U.S. Application Data continuation of application No. PCT/EP2015/080132, filed on Dec. 17, 2015.

(56) References Cited

U.S. PATENT DOCUMENTS

| | | | |
|---|---|---|---|
| 11,099,149 B2* | 8/2021 | Bauer-Espindola | ........................ G01N 27/3272 |
| 2003/0024811 A1 | 2/2003 | Davies et al. | |
| 2003/0098233 A1 | 5/2003 | Kermani et al. | |
| 2003/0109798 A1 | 6/2003 | Kermani | |
| 2004/0118705 A1 | 6/2004 | Khan | |
| 2005/0214171 A1 | 9/2005 | Gerstle et al. | |
| 2005/0279647 A1 | 12/2005 | Beaty | |
| 2006/0175205 A1 | 8/2006 | Cui et al. | |
| 2007/0068807 A1 | 3/2007 | Feldman et al. | |
| 2009/0078030 A1 | 3/2009 | Jung | |
| 2011/0155589 A1 | 6/2011 | Chatelier et al. | |
| 2012/0080326 A1 | 4/2012 | Chatelier et al. | |
| 2013/0026050 A1 | 1/2013 | Harding et al. | |
| 2013/0228475 A1 | 9/2013 | Setford et al. | |
| 2014/0174947 A1 | 6/2014 | Moffat et al. | |
| 2014/0178909 A1 | 6/2014 | Tonks | |

FOREIGN PATENT DOCUMENTS

| | | |
|---|---|---|
| EP | 2138841 A2 | 12/2009 |
| EP | 2282205 A1 | 2/2011 |
| KR | 10-2011-0079561 A | 7/2011 |
| WO | 2000020626 A1 | 4/2000 |
| WO | 2001057238 A2 | 8/2001 |
| WO | 2009/053834 A1 | 4/2009 |
| WO | 2010/052307 A3 | 7/2010 |
| WO | 2012/045425 A1 | 4/2012 |
| WO | 2012/091728 A1 | 7/2012 |
| WO | 2014/198428 A1 | 12/2014 |

OTHER PUBLICATIONS

Hönes, Joachim et al., The Technology Behind Glucose Meters: Test Strips, Diabetes Technology & Therapeutics, 2008, pp. S-10-S-26, vol. 10, Supplement 1.

International Preliminary Report on Patentability dated Jun. 29, 2017, in PCT/EP2015/080132, 14 pages.

Search Report and Written Opinion dated Jun. 1, 2020, in Application No. BR112017011033-4, 4 pp.

* cited by examiner

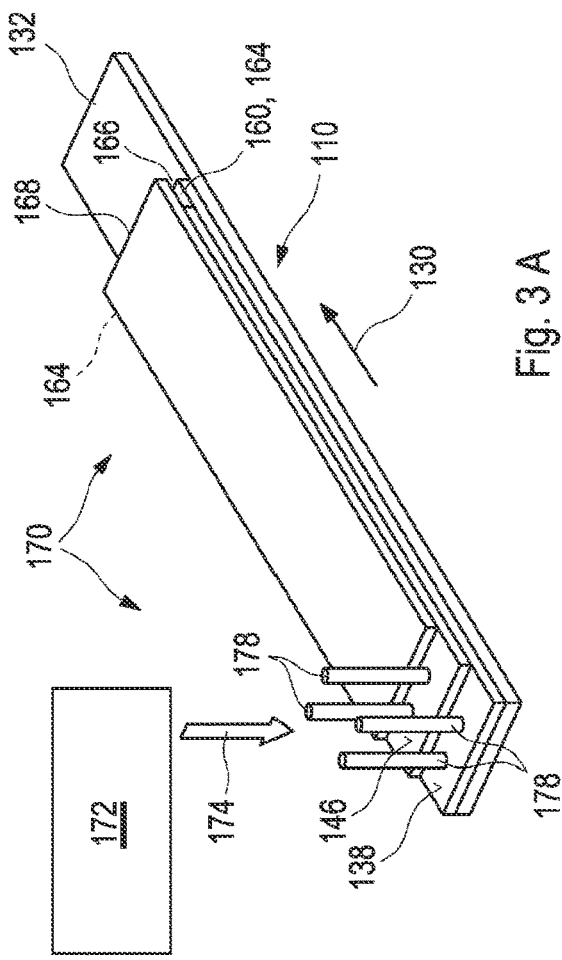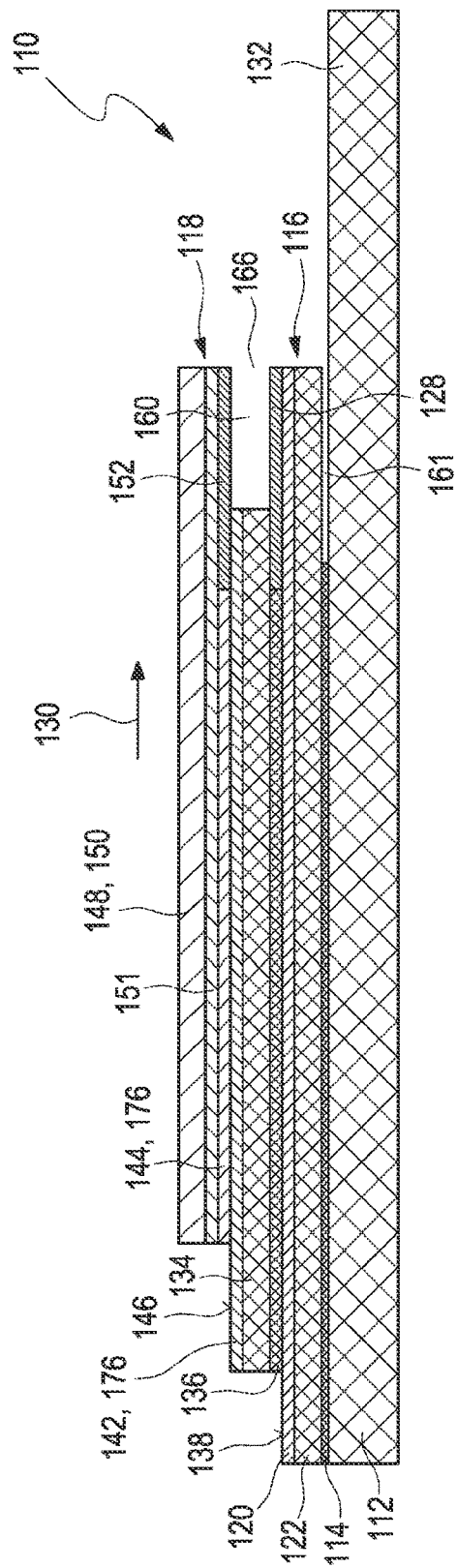

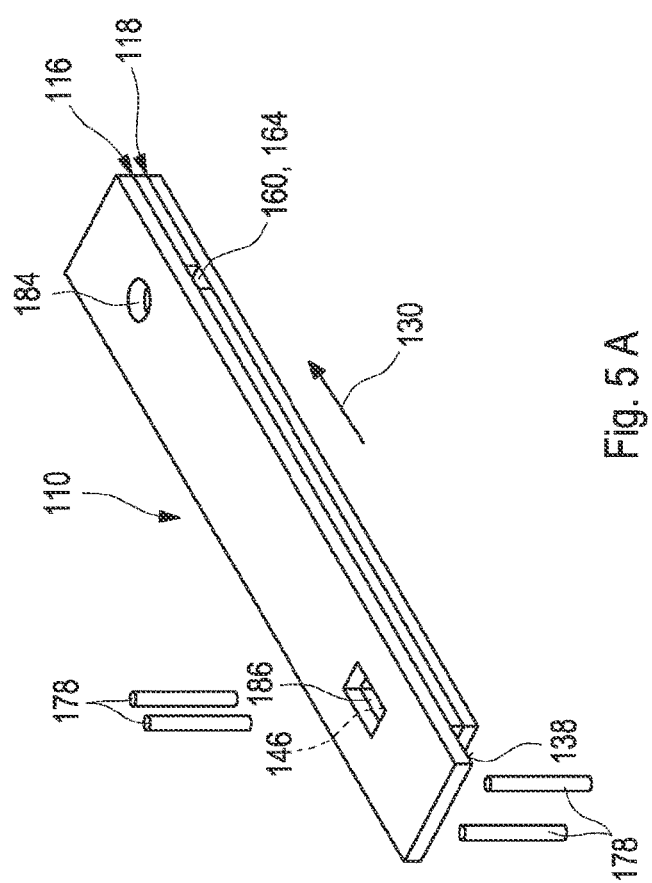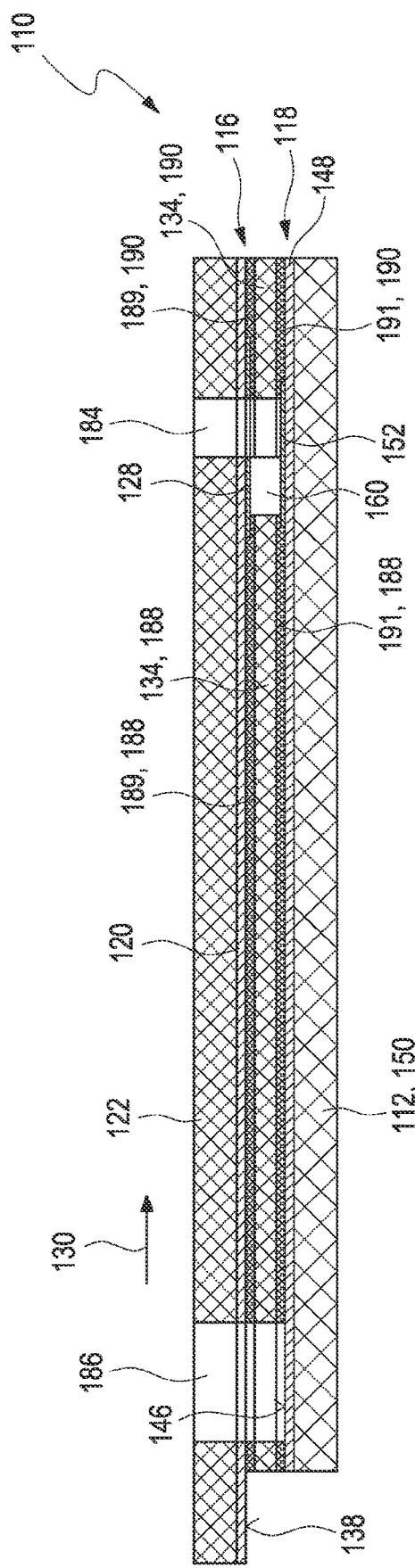

TEST ELEMENT FOR ELECTROCHEMICALLY DETECTING AT LEAST ONE ANALYTE

CROSS-REFERENCE TO RELATED APPLICATIONS

This application is a continuation of U.S. patent application Ser. No. 15/604,017, filed 24 May 2017, which is a continuation of International Patent Application No. PCT/EP2015/080132, filed 17 Dec. 2015, which claims the benefit of European Patent Application No. 14199341.0, filed 19 Dec. 2014, the disclosures of which are hereby incorporated herein by reference in their entirety.

TECHNICAL FIELD

The present disclosure relates to a test element for electrochemically detecting at least one analyte, a method for producing the test element and a system for determining at least one property of a sample. The method and devices according to the present disclosure may be used for detecting at least one analyte present in one or both of a body tissue or a body fluid, in particular the method and devices are applied in the field of detecting one or more analytes such as glucose, lactate, triglycerides, cholesterol or other analytes, typically metabolites, in body fluids such as blood, typically whole blood, plasma, serum, urine, saliva, interstitial fluid or other body fluids, both in the field of professional diagnostics and in the field of home monitoring. However, other fields of application are feasible.

BACKGROUND

In the field of medical technology and diagnostics, a large number of devices and methods for detecting at least one analyte in a body fluid are known. The method and devices may be used for detecting at least one analyte present in one or both of a body tissue or a body fluid, in particular one or more analytes such as glucose, lactate, triglycerides, cholesterol or other analytes, typically metabolites, in body fluids such as blood, typically whole blood, plasma, serum, urine, saliva, interstitial fluid or other body fluids. Further devices are known for measuring activating times, e.g., a thrombin activation time measurement for coagulation monitoring. Without restricting the scope of the present disclosure, in the following, mainly reference is made to the determination of glucose as an exemplary and typical analyte.

The determination of blood glucose concentration as well as a corresponding medication is an essential part of daily routine for many diabetics. In order to increase convenience and in order to avoid restricting the daily routine by more than a tolerable degree, portable devices and test elements are known in the art, such as for measuring blood glucose concentration during work, leisure or other activities away from home. In the meantime, many test devices are commercially available. A large number of test devices and test systems are known that are based on the use of test elements in the form of test strips. Applications are known, in which a multiplicity of test strips is provided by a magazine, wherein a test strip from the magazine automatically may be provided to the testing device. Other applications, however, are known in which single test strips are used, which are inserted into the testing device manually by a user. Therein, typically, the end of the test strip is adapted to be inserted into the testing device and for detecting the analyte, wherein the opposing end of the test strip serves as a handle enabling the user to push the test strip into the testing device or to remove the test strip from the testing device. For applying the sample to the test element, typical test elements provide at least one sample application site, such as a capillary opening in capillary test elements or a spreading layer, i.e., net or mesh-like structure used to spread and/or distribute the sample to what can be underlying layers in optical test strips having a top dosing system. Test strips of this type are commercially available, e.g., under the trade name ACCU-CHEK ACTIVE®. Alternatively to home care applications, such test elements may be used in professional diagnostics, such as in hospital applications.

In many cases, for detecting the analyte, test elements are used, such as test strips, which comprise one or more test fields having one or more test chemistries. The test chemistries are adapted to change one or more detectable properties in the presence of the analyte to be detected. Thus, electrochemically detectable properties of the test chemistry and/or optically detectable properties of the test chemistry may be changed due to the influence of the presence of the analyte. For potential test chemistries that may be used within the present disclosure, reference may be made to J. Hönes et al.: Diabetes Technology and Therapeutics, Vol. 10, Supplement 1, 2008, S-10 to S-26, the disclosure of which is hereby incorporated herein by reference. However, other types of test chemistries may be used within the present disclosure.

In general, the detection of the at least one analyte can be performed by using an electrochemical test element. Commonly used are disposable electrochemical capillary sensor test elements. Such test elements typically comprise at least one working electrode for detecting the analyte as well as at least one counter electrode to support a current flow through a measuring cell of the test element. In addition, optionally, the test element may comprise at least one reference electrode. In alternative embodiments, a reference electrode may be designed individually and/or may be combined with the counter electrode. However, other types of measurement setups are possible, in order to derive an analyte concentration from a comparison of electrode potentials.

Such test elements typically comprise a measuring cell. The measuring cell may be a capillary configured to aspirate a liquid sample embedded between at least two electrode surfaces, in particular of the working electrode and the counter electrode. A voltage between the at least two electrodes may be applied and a responding current is detected and converted into a concentration value of the at least one analyte. Typically, the counter electrode is provided in order to close an electric circuit to the working electrode. For this purpose, typically, redox currents and/or, to a lower extent, capacitive charging currents are used. Typically, the working electrode comprises at least one detector substance adapted to perform an oxidation reaction and/or a reduction reaction with the analyte. In many cases, the detector substance comprises at least one enzyme such as glucose oxidase (GOD). In case the detection reaction comprises an oxidation reaction at the working electrode, the counter electrode typically provides a reduction reaction in order to close the electric circuit.

Specifically, the working electrode may be covered by at least one reagent layer. Often the reagent layer may comprise an enzyme with a redox active enzyme co-factor to support a specific oxidation of the analyte in the body fluid. The reagent layer may comprise further a redox cycle providing substance, which may act as an electron acceptor. The redox cycle providing substance may react with the enzyme co-factor and may transport electrons taken from the enzyme co-factor to the electrode surface by diffusion. At the electrode surface, a redox mediator may be oxidized and the transferred electrons may be detected as a current. The current may be proportional to a concentration of the analyte in the body fluid. When applying the liquid sample to the measuring cell, the reagent may get dissolved and a measuring process can be started by applying the voltage. The voltage is commonly applied to the electrodes by using conductive contact pads arranged at one end of the test strip connected with conductive traces along the test strip.

Generally the working electrode may be designed as in blood glucose test elements, such as test elements commercially available, e.g., under the trade name ACCU-CHEK AVIVA® or the trade name ACCU-CHEK PERFORMA®, or as in coagulation monitoring test elements, such as test strips commercially available, e.g., under the trade name COAGUCHEK®. Thus, a plastic foil may be used as a test carrier, which may be covered with at least one conductive layer building at least one contact, conductive traces and electrode supports. The conductive layer may be sputtered as a thin metal film directly on the test carrier and may be structured by one or more of laser etching, laser ablation or lithography. Alternatively, the structures may be created by screen or inkjet printing processes. The reagent layer may be applied to the test carrier by one or more of coating, printing or dispensing.

The working electrode may be of one or more of a noble metal, such as gold, palladium, platinum, or carbon in form of graphite or glassy carbon. For example, gold is used in ACCU-CHEK AVIVA®, ACCU-CHEK PERFORMA®, and COAGUCHEK® test strips. Firstly, gold is a very expensive material. Further, the counter electrode may even be made from a reducible material. In the art, redox materials such as Ag/AgCl systems are known, such as for combined counter electrodes/reference electrodes. In this case, the available oxidation potential of the gold working electrode versus an Ag/AgCl electrode is limited to about 700 mV and gold will get oxidized at higher voltages, which may cause high, unpredictable background currents.

Alternatively to gold, graphite electrodes may be used. Graphite may be used as a paste or ink, containing also organic components allowing a coating process. Thick graphite films may be structured by screen printing or a similar process. However, the printed graphite electrode surfaces may have relative high tolerances and may cause higher imprecisions compared to a sputtered, laser ablated gold electrode. All types of test elements with electrodes produced in such electrode structuring processes require an exact positioning in lamination processes, wherein the structured test carrier and the capillary structure are assembled. Thus, a manufacturing process of such a test strip may be complex, expensive and inflexible. Further, structures of the test elements, as dimensions of the test elements, are fixed and cannot be changed easily to produce variants of the test strip.

In test elements commonly used, the electrodes may be arranged in a coplanar configuration. Due to manufacturing costs and process complexity, is may be desirable to produce the electrodes during one production process, such as during one lamination process. Samples of the body fluid may be taken by pricking a finger tip by a user, for example in a self-testing or a home care application. These samples may have small volumes, such as volumes smaller than 2 µl. Hence, a capillary volume suitable for these samples has to be small, such that for production reasons it may be only possible to coat the at least two co-planar electrodes with the same reagent stripe in one lamination process. Thus, active ingredients in the reagent must not only support an analytical detection reaction at the working electrode, they also have to support electrode reactions on the counter electrode. However, this may set limits for usable chemistry options: the reagent has to be stable in liquid during a coating process, which may last up to seven days; the reagent must not interfere with redox active substances in the sample; and the working electrode current must not cut off by a limited counter electrode reaction.

An opposing electrode configuration allows the working and the counter electrode to be coated with separate reagents. For example, the counter electrode may be coated with an Ag/AgCl paste. However, the known devices with opposing electrode configurations reveal disadvantages. In particular, coating and drying processes of a manufacturing process of the electrodes cannot be performed together, but have to be performed in parallel or separate process steps. Therefore, the manufacturing process may be complex and thus expensive. Further, the attainable volume of the capillary may be higher compared to strip designs with one reagent stripe.

Further, as outlined above, a required electrode shape and/or structure of known electrodes may be disadvantageous. In A. Heller and B. Feldman: Electrochemistry in Diabetes Management, Accounts of chemical research, Vol. 43, No. 7, July 2010, 963-973, a test strip with an opposing electrode configuration is shown. However, the described test strip requires electrodes with a specific electrode structure. Therefore, an exact positioning is required and thus the manufacturing process may be complex and expensive.

Known test elements for home care and/or self-testing applications may have a front dosing or side dosing position for dosing or application of the sample into the capillary. As outlined above, a sample of the body fluid may be taken by pricking a finger tip. Commonly, capillary openings may be arranged on a front edge or a side edge of the test element. However, for the usage in professional settings, such as in hospitals, a significant part of the overall testing may be from venous or arterial blood taken from sample tubes, so that transfer devices like pipettes, glass capillaries or syringes have to be used for dosing or application of the sample. Thus, capillary openings on the front edge or the side edge may be not convenient and difficult to handle with those transfer devices.

Thus, there is a need in the art for a test element, which can be manufactured in an easy and cost effective process, such as without any positioning dependent alignment required in the whole manufacturing process. Further, a sample dosing to the test elements shall be convenient and easy to handle both in home care and in professional diagnostics applications.

SUMMARY

It is against the above background that the embodiments of the present disclosure provide certain unobvious advantages and advancements over the prior art. In particular, the inventors have recognized a need for improvements in a test element for electrochemically detecting at least one analyte, a method for producing a test element and a system for determining at least one property of a sample.

In accordance with one embodiment of the present disclosure, a system is provided for determining at least one property of a sample, the system comprising at least one test element, wherein the test element comprises at least one first electrode and at least one second electrode, wherein the first electrode is designed as a working electrode and the second electrode is designed as a counter electrode, wherein the test element comprises at least one capillary capable of receiving a sample of the body fluid, wherein the first electrode and the second electrode are arranged on opposing sides of the capillary, wherein the first electrode and the second electrode and the capillary in between the first electrode and the second electrode form an electrochemical cell, wherein the test element is configured to detect the at least one analyte independently of a filling level of the electrochemical cell, wherein the first electrode and the second electrode are arranged such that during a capillary filling the first electrode and the second electrode are wetted simultaneously and at an equal rate, the system further comprising at least one measurement device adapted for performing at least one electrical measurement using the test element, wherein the measurement device is configured to detect both an AC signal and a DC signal, and wherein the measurement device is configured to detect the at least one analyte independently of a filling level of the electrochemical cell.

In accordance with another embodiment of the present disclosure, a method for determining at least one property of a sample is provided, wherein a system according to an embodiment of the disclosure is used, and wherein the method comprises the following steps: a) connecting the test element to at least one measurement device; b) applying a sample of bodily fluid to a capillary of at least one test element; c) determining both an AC signal and a DC signal with said measurement device; and d) calibrating measurement results by using the AC and DC signal.

In accordance with yet another embodiment of the present disclosure, a test element for electrochemically detecting at least one analyte in a bodily fluid is provided, wherein the test element comprises at least one first electrode and at least one second electrode, wherein the first electrode is designed as a working electrode and the second electrode is designed as a counter electrode, wherein the test element comprises at least one capillary capable of receiving a sample of the body fluid, wherein the first electrode and the second electrode are arranged on opposing sides of the capillary, wherein the first electrode and the second electrode and the capillary in between the first electrode and the second electrode form an electrochemical cell, wherein the test element is configured to detect the at least one analyte independently of a filling level of the electrochemical cell, wherein the first electrode and the second electrode are arranged such that during a capillary filling the first electrode and the second electrode are wetted simultaneously and at an equal rate, wherein the capillary is open at three sides, wherein a sample of bodily fluid is applicable to one or both of a side dose position or a front dose position, wherein the test element comprises a first electrode contact zone and a second electrode contact zone configured to contact the first electrode and the second electrode with a further device, wherein the first electrode contact zone and the second electrode contact zone are arranged in different layers of a layer setup of the test element, wherein one of the first electrode contact zone and the second electrode contact zone protrudes over the other one of the first electrode contact zone and the second electrode contact zone, wherein the first electrode contact zone and the second electrode contact zone are configured to be electrically contacted from opposing sides of the test element, wherein the test element comprises a layer setup, wherein the first electrode comprises at least one first electrode conductive layer disposed on at least one first electrode carrier layer, wherein the second electrode comprises at least one second electrode conductive layer disposed on at least one second electrode carrier layer, and wherein at least one spacer layer is disposed in between the first electrode conductive layer and the second electrode conductive layer.

In accordance with still another embodiment of the present disclosure, a method for producing a test element according to an embodiment of the present disclosure is provided, the method comprising at least one step of forming a layer setup, wherein the first electrode, the second electrode and the capillary are formed such that the first electrode and the second electrode are arranged on opposing sides of the capillary, wherein the test element is produced in a continuous process and the method further comprising cutting the layer setup into test strips.

These and other features and advantages of the embodiments of the present disclosure will be more fully understood from the following description in combination with the drawings and accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present disclosure can be best understood when read in conjunction with the following drawings, where like structure is indicated with like reference numerals and in which:

FIG. 3A shows a system according to the present disclosure and a perspective, cross-sectional view of the test element;

FIG. 3B shows another view of a system according to the present disclosure and a cross-section of the test element;

FIG. 5A shows a second embodiment of a test element according to the present disclosure;

FIG. 5B shows a cross-section of the second embodiment of the test element;

Figure 1:
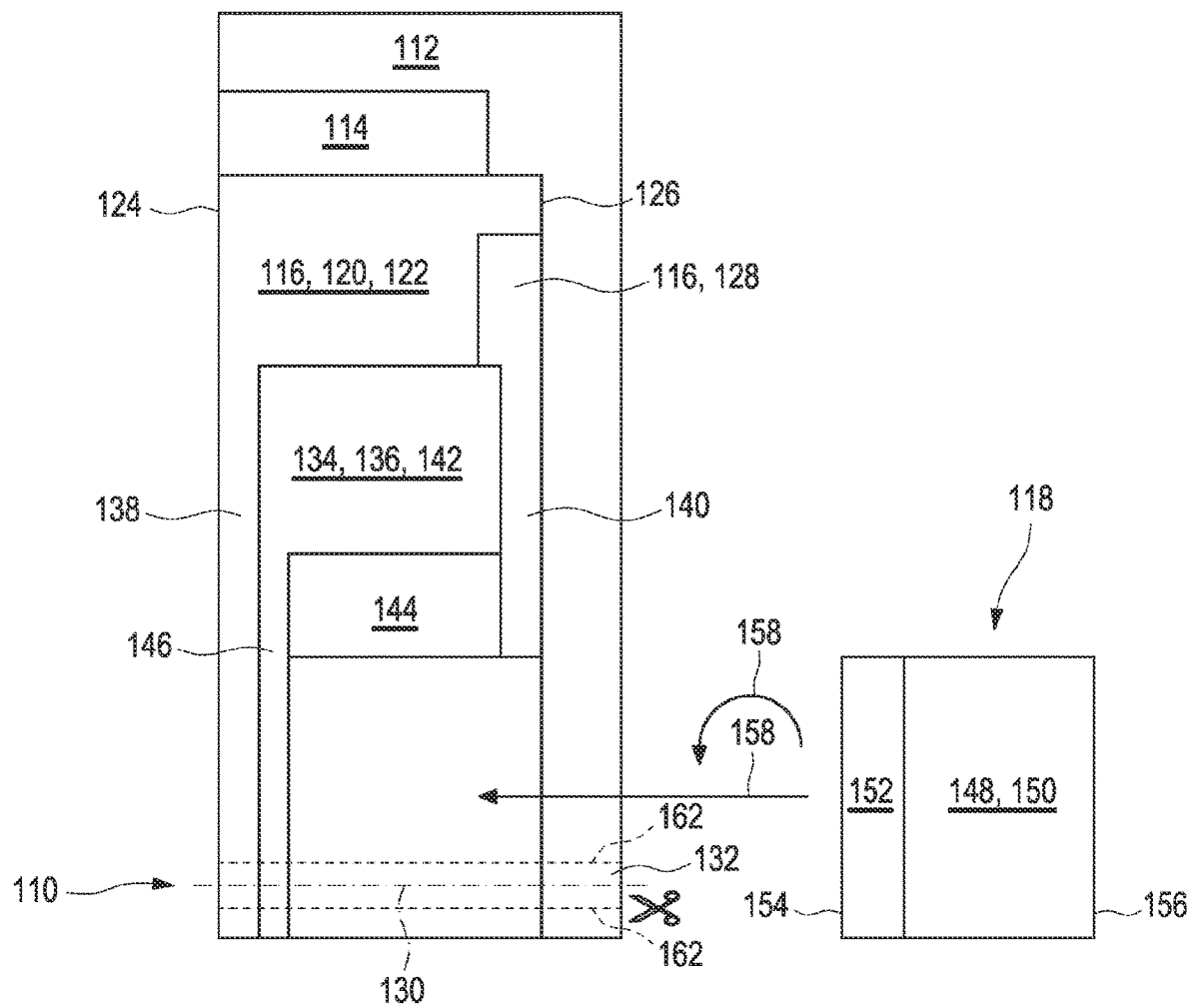
FIG. 1 shows a layer setup of an embodiment of a test element according to the present disclosure.

Skilled artisans appreciate that elements in the figures are illustrated for simplicity and clarity and have not necessarily been drawn to scale. For example, the dimensions of some of the elements in the figures may be exaggerated relative to other elements to help improve understanding of the embodiment(s) of the present disclosure.

DETAILED DESCRIPTION

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e., a situation in which A solely and exclusively consists of B) and to a situation in which, besides B, one or more further elements are present in entity A, such as element C, elements C and D or even further elements.

Further, as used in the following, the terms "preferably", "more preferably", "particularly", "more particularly", "specifically", "more specifically" or similar terms are used in conjunction with optional features, without restricting alternative possibilities. Thus, features introduced by these terms are optional features and are not intended to restrict the scope of the claims in any way. The invention may, as the skilled person will recognize, be performed by using alternative features. Similarly, features introduced by "in an embodiment of the disclosure" or similar expressions are intended to be optional features, without any restriction regarding alternative embodiments of the disclosure, without any restrictions regarding the scope of the disclosure and without any restriction regarding the possibility of combining the features introduced in such way with other optional or non-optional features of the disclosure.

In accordance with an embodiment of the present disclosure, a test element for electrochemically detecting at least one analyte of a bodily fluid is disclosed. As further used herein, the term "analyte" may refer to an arbitrary element, component or compound, which may be present in a body fluid and the concentration of which may be of interest for a user or a patient. Typically, the analyte may be or may comprise an arbitrary chemical substance or chemical compound that may take part in the metabolism of the patient, such as at least one metabolite. As an example, the at least one analyte may be selected from the group consisting of glucose, cholesterol, triglycerides, lactate. Additionally or alternatively, however, other types of analytes may be used and/or any combination of analytes may be determined. Generally, an arbitrary type of body fluid may be used. As generally used within the present disclosure, the term "patient" may refer to a human being or an animal, independent from the fact that the human being or animal, respectively, may be in a healthy condition or may suffer from one or more diseases. As an example, the patient may be a human being or an animal suffering from diabetes. However, additionally or alternatively, the invention may be applied to other types of users or patients.

The body fluid may be a body fluid that is present in a body tissue of the patient, such as in the interstitial tissue. Thus, as an example, the body fluid may be selected from the group consisting of blood and interstitial fluid. However, additionally or alternatively, one or more other types of body fluids may be used. The body fluid generally may be contained in a body tissue.

As used herein, the term "test element" refers to an arbitrary device that is capable of detecting the analyte in the body fluid, typically by comprising at least one component that changes at least one detectable property when the analyte is present in the body fluid, such as a test chemistry, for example one or more known test chemistries disclosed in the prior art. The term "test chemistry" refers to an arbitrary material or a composition of materials adapted to change at least one detectable property in the presence of the at least one analyte. Generally, this property may be selected from an electrochemically detectable property and/or an optically detectable property, such as a color change and/or a change in remissive properties. Specifically, the at least one test chemistry may be a highly selective test chemistry, which only changes the property if the analyte is present in a sample of a body fluid applied to the test element, whereas no change occurs if the analyte is not present. More typically, the degree or change of the at least one property is dependent on the concentration of the analyte in the body fluid, in order to allow for a quantitative detection of the analyte. As an example, the test chemistry may comprise at least one enzyme, such as glucose oxidase and/or glucose dehydrogenase. Additionally or alternatively, the test chemistry may comprise one or more co-enzymes and/or one or more mediators. Further, alternatively or additionally, the test chemistry may comprise one or more dyes, which, typically in interaction with the one or more enzymes, may change their color in the presence of the at least one analyte to be detected.

As used herein, the term "electrochemically detection" refers to a detection of an electrochemically detectable property of the analyte, such as an electrochemical detection reaction. Thus, for example, the electrochemical detection reaction may be detected by comparing one or more electrode potentials, such as an electrostatic potential of a working electrode with the electrostatic potential of one or more further electrodes such as a counter electrode or a reference electrode. The detection may be analyte specific. The detection may be a qualitative and/or a quantitative detection. The test element may be a strip-shaped test element.

As used herein, the term "strip-shaped" refers to an element having an elongated shape and a thickness, wherein an extension of the element in a lateral dimension exceeds the thickness of the element, such as by at least a factor of 2, typically by at least a factor of 5, more typically by at least a factor of 10, and most typically by at least a factor of 20 or even at least a factor of 30. The test element may be a test strip.

The test element comprises at least one first electrode and at least one second electrode. The first electrode is designed as a working electrode and the second electrode is designed as a counter electrode. As used herein, the term "electrode" refers to an entity of the test element that is adapted to get in contact with the body fluid, either directly or via at least one semipermeable membrane or layer. Each electrode may be embodied such that an electrochemical reaction may take place at the electrode. Thus, the electrodes may be embodied such that an oxidation reaction and/or a reduction reaction may take place at the electrodes. As used herein, the term "working electrode" refers to an electrode being adapted for performing at least one electrochemical detection reaction for detecting the at least one analyte in a body fluid. Thus, the working electrode may comprise at least one reagent, such as one test chemistry. As used herein, the term "counter electrode" refers to an electrode adapted for performing at least one electrochemical counter reaction adapted for balancing a current flow required by the detection reaction at the working electrode. The test element may further comprise at least one reference electrode, for example a combined counter electrode/reference electrode system. As used herein, the term working electrode refers to an electrode being adapted for performing at least one electrochemical detection reaction for detecting the at least one analyte in a body fluid.

The first electrode and the second electrode may have the same dimension. The term "dimension" refers to one or more of a width, a length, a surface area, and a shape of the first and the second electrodes. In particular, the first and the second electrodes may be designed with a non-structured electrode shape, such as a shape without structures such as inlets, notches, etc. The shape of the electrodes may be determined by a manufacturing process, such as a cutting process. Thus, the shape may be essentially rectangular, wherein the term "essentially rectangular" refers to that within tolerances of manufacturing deviations from a rectangular shape are possible.

The first electrode and the second electrode may be made of a non-corrosive and non-passivating material.

The first electrode may comprise at least one electrode conductive layer and at least one reagent coating in contact with the first electrode conductive layer. The term "electrode conductive layer" refers to a layer with electrically conductive properties. The term "electrically conductive" refers to an electric conductivity, typically given in S/m or 1/Ωm of at least $10^0$ S/m, typically of at least $10^3$ S/m and, more typically, of at least $10^5$ S/m. The first electrode conductive layer may comprise at least one of: a metal layer, in particular a noble metal layer selected from the group consisting of palladium, silver or gold; a conductive carbon layer, in particular a carbon paste layer. However, other types of metals may be used in addition or alternatively. As used herein, the term "paste" refers to an amorphous substance containing one or more particulate components, such as one or more conductive components and/or powders, as well as one or more binder materials, such as one or more organic binder materials. Additionally or alternatively, the first electrode conductive layer may comprise an aluminum layer, such as a sputtered aluminum layer, combined with a conductive carbon paste.

The first electrode conductive layer may be disposed on a first electrode carrier layer, typically a first electrode carrier foil. In one embodiment, the first electrode carrier layer may be coated with a conductive carbon paste, typically homogenously. Alternatively, as outlined above, the first electrode carrier layer may be coated, e.g., with gold or gold on palladium, etc. The test element may be produced in a continuous tape manufacturing process. Thus, the coated layer may be coated as thin as possible such that a multi-layer winding up of the continuous tape on a reel in a manufacturing process is possible. The first electrode may have a multi-layer setup. As used herein, the term "electrode carrier layer" refers to an element of the first electrode onto which further layers or elements of the first electrode can be applied. In general, the electrode carrier layer may have an arbitrary shape, such as a strip-shape. The first electrode carrier layer may comprise a flexible substrate, such as a plastic material and/or a laminate material and/or a paper material and/or a ceramic material. The electrode carrier layer may comprise a foil, in particular a polymeric foil. The first electrode conductive layer may extend from a first longitudinal edge of the first electron carrier layer to a second longitudinal edge of the first electrode carrier layer. The first electrode conductive layer may fully cover the first electrode carrier layer. Thus, a width of the first electrode conductive layer corresponds to a width of the first electrode carrier layer, wherein the term "width" of the first electrode carrier layer and the first electrode conductive layer refers to a maximum extension perpendicular to an elongated test element direction. However, as will be outlined below, embodiments are typical, wherein a length of the first electrode conductive layer may be different to a length of the first electrode carrier layer, in particular such that a handle length of the first electrode conductive layer may be shorter than the length of the first electrode carrier layer such that a handle of the test element may be formed.

The reagent coating may comprise at least one reagent stripe coated onto the first electrode conductive layer. In one embodiment, the reagent stripe may be coated onto the first electrode carrier layer. The reagent stripe material may comprise at least one detector substance to perform an electrically detectable electrochemical detection reaction with the analyte. The at least one detector substance may comprise one or more enzymes, such as glucose oxidase (GOD) and/or glucose dehydrogenase (GDH), typically an enzyme which, by itself and/or in combination with other components of the detector substance, typically is adapted to perform an oxidation and/or reduction reaction with the at least one analyte to be detected. The reagent stripe material may further comprise one or more auxiliary components, such as one or more co-enzymes and/or may comprise one or more mediators that may be adapted for an improved charge transfer from one component of the detection reaction to another component. The reagent stripe may be coated homogenously onto the first electrode conductive layer. The coating may be performed in a die coating process in at least one coating device followed by a drying process by running through at least one drier.

The second electrode may comprise at least one second electrode conductive layer. The second electrode conductive layer may comprise at least one of: a metal layer, typically a metal layer selected from the group consisting of palladium, silver or gold; a conductive carbon layer, in particular a carbon paste layer. The second electrode may further comprise Ag/AgCl, in particular an Ag/AgCl paste. The Ag/AgCl paste may be coated onto the second electrode conductive layer such that an area coated with the Ag/AgCl paste may face the reagent coating of the first electrode conductive layer. The second electrode conductive layer may be disposed on a second electrode carrier layer, typically a second electrode carrier foil. The second electrode carrier foil may be designed as a cover foil of the test element. In one embodiment, the second electrode carrier layer may be coated with a silver layer, for example, the second electrode carrier layer may be sputtered with a silver layer. The second electrode conductive layer may extend from a first longitudinal edge of the second electrode carrier layer to a second longitudinal edge of the second electrode carrier layer. The second electrode conductive layer may fully cover the second electrode carrier layer. Thus, a width of the second electrode conductive layer corresponds to a width of the second electrode carrier layer, wherein the term "width" of the second electrode carrier layer and the second electrode conductive layer refers to a maximum extension perpendicular to an elongated test element direction.

The test element comprises at least one capillary capable of receiving a sample of the body fluid. As used herein, the term "capillary" refers to an element which is adapted to receive the sample of the body fluid and/or transport the sample of the body fluid by capillary forces. The capillary element may comprise at least one volume configured to receive the sample of the body fluid, e.g., one or more capillary caps and/or one or more capillary slots and/or one or more capillary tubes having an arbitrary cross-section, such as a rectangular cross-section and/or a rounded cross-section and/or a polygonal cross-section.

The first electrode and the second electrode are arranged on opposing sides of the capillary. The first and the second electrode are arranged as opposing electrodes, such that a surface of the first electrode faces a surface of the second electrode. The first electrode and the second electrode are arranged such that during a capillary filling the first electrode and the second electrode are wetted simultaneously and at an equal rate. An increment of a wetted surface area $dA1$ of the first electrode per increment $dV$ of a filled volume of the capillary at all times may equal an increment of a wetted surface area $dA2$ of the second electrode. Consequently, as used herein, the term "wetting at an equal rate", in this context, generally refers to the fact that $dA1/dV=dA2/dV$, i.e., that the ratios of the wetted surface area and the filled volume are equal for both electrodes, at least after a time required for reaching an equilibrium state. The time dependency of the wetting, however, not necessarily is equal, i.e., the equation $dA1/dt=dA2/dt$ may be true for all times but may also not be true for all points in time. The first electrode and the second electrode may be aligned in parallel, in particular as surfaces that are parallel to each other at least in the direction defined by the length of the capillary. Further, as outlined above, the first and the second electrode may have the same dimensions and may have a non-structured shape. The first electrode may extend over a full length of the capillary. The second electrode may extend over a full length of the capillary. As used herein, the term "length of the capillary" refers to a maximum extension of the capillary in one dimension within the test element. In one embodiment, the capillary may extend perpendicular to the elongated test element direction such that in this case the length of the capillary refers to a maximum extension of the capillary perpendicular to the elongated test element direction. In an alternative embodiment, the capillary may extend along the elongated test element direction such that in this case the length of the capillary refers to a maximum extension of the capillary along the elongated test element direction.

The first electrode and the second electrode are arranged such that during a capillary filling the first electrode and the second electrode are wetted simultaneously. An increment of a wetted surface area $dA1$ of the first electrode per increment $dV$ of a filled volume of the capillary at all times may equal an increment of a wetted surface area $dA2$ of the second electrode. As used herein, the term "capillary filling" refers to a process of receiving the sample of the body fluid.

The first electrode and the second electrode and the capillary in between the first electrode and the second electrode form an electrochemical cell, wherein the test element is configured to detect the at least one analyte independently of a filling level of the electrochemical cell. The electrochemical cell may extend over the full length of the capillary. Hence, the first electrode and the second electrode may extend over the full length of the capillary.

The sample of the body fluid may be applicable to one or more of: a side dose position, a top dose position, and a front dose position. As used herein, the term "side dose position" refers to a position on an elongated edge of the test element where the sample of the body fluid is applicable, e.g., the test element may comprise at least two opposing openings at edges of the test element. A side dose position may be an ideal application position for capillary blood from a finger stick. As used herein, the term "top dose position" refers to a position where the sample of the body fluid can be applied from above through a layer set-up of the test element into the capillary. The test element may comprise a top dose position and further a through hole extending through a cover foil into the capillary. As used herein, the term "cover foil" refers to an element of the test element confining a layer setup of the test element, e.g., a top foil. The cover foil may be configured as the first electrode carrier layer or the second electrode carrier layer. The through hole may be positioned such that the through hole may touch the capillary at one edge of at least one capillary wall. A top dose position may be an ideal application position for dosing the sample with a transfer device, e.g., a pipette. Further, in case the test element comprises at least one top dose position, it may be possible to close the capillary on all sides if an appropriate venting of the capillary space is possible, e.g., via a venting element, e.g., a small vent hole opening or a venting membrane. As used herein, the term "front dose position" refers to a position at a front face of the test element, wherein the term "front face" refers to a front surface area of a width of the test element. For example, the front dose position may be an open side at the front face. The side dose position, the top dose position and the front dose position may be positioned at a distance to a region of the test element inserted into a further measurement device, e.g., a meter, such that no sample is transferred into the further measurement device. This is advantageous under hygienic aspects and cleaning and disinfection requirements.

The test element may have an elongated shape extending along a longitudinal axis, wherein the capillary at least partially extends along the longitudinal axis of the test element. The term "at least partially extending along the longitudinal axis" refers to embodiments wherein the capillary may fully extend along the longitudinal axis and/or embodiments wherein parts of the capillary may not extend along the longitudinal axis. In particular, this embodiment may be used if testing times significantly longer than a minute, e.g., testing times of more than 5 minutes, are required, because the sample within the capillary will not dry off. Further, this embodiment may be used in case the sample has to be transported to a further device, e.g., to a heating device, typically a thermostatic controlled heating device within the meter, in case test parameters might need to be heated up to a temperature above the surrounding temperature. The test element may comprise a region insertable into the further device. The capillary may comprise a vent hole opening, such as a vent hole opening at an end of the capillary in the direction of the insertable region. In this embodiment, the first electrode may comprise a second reagent coating in the direction of the insertable region, which may create a hydrophobic surface. The hydrophobic surface may hinder the passage of the sample of the body fluid up to the vent hole, and thus contaminate the further device. To ensure a reliable and quick sample transport, in general, capillary walls may be hydrophilic. Thus, surfaces of the capillary walls may be treated with at least one detergent and/or with at least one surfactant, in particular the surfaces of the first electrode and the second electrode, which are arranged on opposing sides of the capillary.

The test element may have an elongated shape extending along a longitudinal axis, wherein the capillary at least partially extends perpendicular to the longitudinal axis. The term "at least partially extending perpendicular to the longitudinal axis" refers to embodiments wherein the capillary may fully extend perpendicular to the longitudinal axis and/or embodiments wherein parts of the capillary may not extend perpendicular to the longitudinal axis. The capillary may extend from a first opening at a first longitudinal edge of the test element to a second opening at a second longitudinal edge of the test element. The capillary may have an open side at a front face of the test element. The test element may have a front dose position located at the front face of the test element. The capillary may comprise a vent hole.

The test element may comprise a side dose position located on one or both of the first opening or the second opening. In one embodiment, the capillary may be open at three sides. The capillary may comprise three openings for receiving the sample of the body fluid, for example, the capillary can receive the sample from at least two side dose positions such as opposing openings of the capillary on opposing edges of the test element, and a third dose position such as a top opening or a front opening. If the test element comprises a side dose position and, therefore, a first opening and the second opening, one of these openings may be used for sample dosing and the other opening has the function of a vent hole opening. In this embodiment, no separate vent hole opening is necessary.

At least one wall of the test element located outside the capillary but next to the opening for receiving the sample of the body fluid may be at least partially coated by at least one hydrophobic coating. The hydrophobic coating may avoid an outspreading of the sample of the body fluid outside the capillary and therefore may support the filling of the capillary. For example, a hydrophobic coating may be applied on top of the second electrode carrier layer, e.g., at the top dose position, and/or in front of the first electrode carrier layer.

The test element may comprise a strip handle. As used herein, the term "strip handle" refers to an element of the test element configured to avoid getting in contact with the sample of the body fluid, such as when handling the test element, e.g., when taking the test element out of a storage vial, inserting the test element into the further device, or pulling out the test element from the further device. The test element may comprise a layer setup disposed on top of at least one carrier element, wherein the carrier element, in a longitudinal direction of the test element, protrudes from the layer setup, thereby forming the strip handle.

The test element may comprise at least one carrier element. As used herein, the term "carrier element" refers to an arbitrary element comprising one or more components. The carrier element may be adapted to carry other components of the test element, such as the at least one test field. Thus, the carrier element may comprise a single-layer set-up of a multi-layer set-up, such as a laminate set-up. The carrier element may comprise one or more materials, such as plastic materials, and/or paper materials, and/or cardboard-materials, and/or ceramic materials. Most typically, the carrier element may comprise a flexible substrate, e.g., one or more plastic materials selected from the group consisting of: a polycarbonate, a polyethylene, a polyethylene terephthalate, and an acrylonitrile-butadiene-styrene. However, in addition or alternatively, other plastic materials are applicable. Additionally or alternatively, the carrier element may comprise one or more metallic materials such as aluminum. Further, combinations of materials are possible, such as laminate materials, wherein the combinations may comprise two or more different types of materials, such as a combination of plastic materials and metallic materials, such as in a layer setup. In general, the carrier element may have an arbitrary shape, such as a strip-shape. The at least one carrier foil may be a polymer foil. The at least one carrier foil may be configured to provide a stability of the test element.

The test element may comprise a first electrode contact zone and a second electrode contact zone configured to contact the first electrode and the second electrode with the further device, in particular a meter. In one embodiment, the first electrode contact zone and the second electrode contact zone may be configured to be electrically contacted from the same side of the test element. The first electrode contact zone and the second electrode contact zone may be arranged in different layers of a layer setup of the test element, wherein one of the first electrode contact zone and the second electrode contact zone may protrude over the other one of the first electrode contact zone and the second electrode contact zone. The first electrode contact zone and the second electrode contact zone may form different steps of a staircase configuration of the layer setup. For example, the first electrode contact zone and the second electrode contact zone may be two rectangular zones at one end of the test element. The first and second electrode contact zones may each be hit upon by at least one connector of the further device, e.g., meter connector pins. The further device may have two pairs of connectors, one pair for each of the first and the second electrode. One connector of each connector pair may be configured to support a current flow through the test element. The other connector may be used to detect a voltage. Such a configuration, also called 4-wire-technique, may allow an electronic controller of the further device to compensate voltage drop induced by parasitic transfer resistances at connection spots of the first and second electrode contact zones and the connectors. However, as the first electrode and the second electrode may be configured as opposing electrodes, to allow an electrical contact from the same side of the test element, the first electrode or the second electrode may be electrically contacted by at least one electrically conductive turnover element, as will be outlined in detail below.

In one embodiment, the first electrode contact zone and the second electrode contact zone may be configured to be electrically contacted from opposing sides of the test element. The first electrode may be contacted through the first electrode contact zone protruding out of the test element layer setup. A punched hole through the cover foil and the spacer foil may be configured as the second electrode contact zone, in particular a contact hole. Thus, no additional electrically conductive turnover element may be required as for the same side contact as outlined above. The first and second electrode contact zones may be hit upon by the at least one connector of the further device, e.g., meter connector pins. Typically, the further device may have two pairs of connectors, one pair for each of the first and the second electrode. One pair of connectors may contact one of the first or second electrodes from one side of the test element, whereas the other pair may contact the other one of the first or second electrode from an opposing side of the test element.

One or both of the first electrode or the second electrode may be electrically contacted by at least one electrically conductive turnover element, wherein the first or second electrode, respectively, may be oriented to face a first direction, wherein the electrically conductive turnover element may be contactable from a second direction, the second direction being an opposite direction of the first direction. The electrically conductive turnover element may comprise at least one of an electrically conductive layer or an electrically conductive foil having a first section and a second section, the first section electrically contacting the first or second electrode, respectively, and the second section being electrically contactable. For example, the electrically conductive turnover element may be configured as a conductive adhesive layer. The electrically conductive turnover element may be partially covered by at least one layer comprising the first or second electrode, respectively, wherein the second section may be located in an uncovered region. As used herein, the term "partially covered" refers to that parts of the electrically conductive turnover element may be covered by the at least one layer comprising the first or second electrode and parts of the electrically conductive turnover element may be uncovered. The electrically conductive turnover element may be laminated to the first or second electrode, respectively.

The test element may comprise a layer setup, wherein the first electrode may comprise at least one first electrode conductive layer disposed on at least one first electrode carrier layer, wherein the second electrode may comprise at least one second electrode conductive layer disposed on at least one second electrode carrier layer. The layer setup may be arranged such that the first electrode conductive layer faces the second electrode conductive layer, with the capillary in between. At least one spacer layer may be disposed in between the first electrode conductive layer and the second electrode conductive layer. Further, the layer setup may comprise at least one adhesive layer. A height of the electrochemical cell may be defined by a thickness of the spacer layer and of adhesive layers in between the first and second electrode. Embodiments are feasible, wherein the at least one adhesive layer may be arranged between the carrier element and the first electrode carrier layer, and/or between the reagent coating and the spacer layer. For example, in case the at least one adhesive layer may be arranged between the carrier element and the first electrode carrier layer, the at least one adhesive layer may be positioned such that a region defined by a position of the electrochemical cell is not covered by the adhesive layer such that a gap between the carrier element and the first electrode may be formed. Thus, in case a user may inadvertently bend the test element, a distance between the first and the second electrode surfaces may remain unaffected. Further, the at least one adhesive layer may be a conductive adhesive layer, e.g., a silver-based adhesive, which may be arranged between the cover foil and the second electrode conductive layer and/or the second electrode conductive layer and the spacer layer. However, other arrangements of adhesive layers may be feasible.

The test element may comprise a layer setup. The working electrode may comprise at least one first electrode conductive layer. The first electrode conductive layer may comprise a carbon ink coating. The first electrode conductive layer may be disposed on at least one first electrode carrier layer. The first electrode carrier layer may be a foil, e.g., a top foil. The working electrode may comprise at least one reagent coating, e.g., a detection reagent coating, in contact with the first electrode conductive layer. The reagent coating may cover at least partially the first electrode conductive layer. The counter electrode may comprise at least one second electrode conductive layer. The second electrode conductive layer may comprise a carbon ink coating. The second electrode conductive layer may be disposed on at least one second electrode carrier layer. The second electrode carrier layer may be a foil, e.g., a bottom foil. The counter electrode may comprise at least one reagent coating in contact with the second electrode conductive layer. The reagent coating may comprise a redox chemistry. The reagent coating may comprise an Ag/AgCl ink. The reagent coating may cover at least partially the second electrode conductive layer. The reagent coating of the working electrode and the counter electrode may cover equal areas of the respective electrode conductive layers. At least one spacer layer may be disposed in between the first electrode conductive layer and the second electrode conductive layer. Adhesive layers may be applied to one or both sides of the spacer layer. Thus, the first electrode conductive layer and the second electrode conductive layer may be fixed within the layer setup by the spacer layer. The first electrode and the second electrode and the capillary in between the first electrode and the second electrode form an electrochemical cell. The electrochemical cell may extend over the full length of the capillary. The first electrode and the second electrode may extend over the full length of the capillary. The spacer layer may be arranged such that it does not extend over the full length of the test element. For example, the spacer layer may cover the capillary partly. The capillary may be open at three sides. The sample of bodily fluid may be applicable to a side dose position and a front dose position.

Further, the test element may comprise a first electrode contact zone and a second electrode contact zone configured to contact the working electrode and the counter electrode with a further device. The first electrode contact zone and/or the second electrode contact zone, and the side and front dose positions, may be arranged at opposing ends of the test element. The first electrode contact zone and the second electrode contact zone may be arranged in different layers of the layer setup of the test element. The first electrode contact zone and the second electrode contact zone may be configured to be electrically contacted from opposing sides of the test element, for example, at top and at bottom sides of the test element. The first electrode conductive layer and the first electrode carrier layer may form an overhang on the contact side of the test element over the second electrode conductive layer and the second electrode carrier layer. Thus, parts of the first electrode conductive layer may be exposed and may allow contacting the working electrode with the further device. As described above, the spacer layer may be arranged such that it does not extend over the full length of the test element. The spacer layer may comprise at least one hole and/or at least one recess, which may have an arbitrary form, for example circular or rectangular. The spacer layer may be formed in one part or in multiple parts. The second electrode contact zone may be formed in the following way: The first electrode conductive layer and the first electrode carrier layer may comprise at least one hole and/or at least one recess, which may have an arbitrary form, for example circular or rectangular. For example, the at least one recess in the first electrode conductive layer and the first electrode carrier layer may be formed by cutting and/or punching. The spacer layer may be arranged such that, within the layer setup of the test element, the spacer layer may not cover the at least one hole and/or at least one recess of the first electrode conductive layer and the first electrode carrier layer. For example, the at least one recess in the spacer layer may be formed by cutting and/or punching. Thus, parts of the second electrode conductive layer may be exposed and may allow contacting the counter electrode with the further device.

In accordance with another embodiment of the present disclosure, a method for producing a test element, disclosed in one or more of the embodiments above or disclosed in further detail below, is disclosed. The method comprises at least one step of forming a layer setup. The first electrode, the second electrode and the capillary are formed such that the first electrode and the second electrode are arranged on opposing sides of the capillary. For a description of possible embodiments and definitions of the test element, reference can be made to the above-mentioned test element according to the present disclosure.

The method may comprise the method steps disclosed in further detail below. The method steps, as an example, may be performed in the given order. However, a different order is also feasible. Further, one or more or even all of the method steps may be performed in parallel or in a timely overlapping fashion. Further, one or more or even all of the method steps may be performed once or repeatedly.

In a particular embodiment, the test element may be a test strip, e.g., the test element has a strip-shape, in particular a rectangular base area.

The test element may be produced in a continuous process. As used herein, the term "continuous process" refers to an arbitrary process in which, by contrast with batch-to-batch processes, production proceeds successively and without interruption of a supporting tape, e.g., a carrier tape. The continuous process may be a reel-to-reel process. For example, the supporting tape may be provided from a starting roller and may be wound up onto a further roller after laminating further tapes onto it.

The step of forming the layer setup may comprise at least one lamination step, wherein in the lamination step at least two layers are combined by a lamination process. The lamination step may comprise a lamination of at least two tapes. The layer setup may comprise the above described elements of the test elements such as one or more of the carrier element, the first electrode, the second electrode, the spacer layer, and at least one adhesive layer.

The method further may comprise cutting the layer setup into test strips. The layer setup may be a tape-shaped layer setup, wherein a width of the tape-shaped layer setup defines a length of the test strips. The length of the test strip may be understood as maximum extension of the test trip in an elongated direction. The width of the laminated tapes may be understood as maximum extension in a dimension perpendicular to a tape elongation direction, wherein in the tape elongation direction the extension of the tape exceeds an extension perpendicular to a tape elongation direction, typically by at least a factor of 3, at least a factor of 10, or even at least a factor of 100. The term "cutting" may be understood as dividing the laminated tape into separated test strips, such that the separated test strips may be used individually. The layer setup, e.g., the laminated tape, may have a length allowing for cutting several test strips, typically 10 or more, more typically 20 or more, and most typically 50 test strips or more, from one tape. The cutting may be performed by a cutting device. Such a strip design made from an endless unstructured tape may be advantageous because the strip length and width can easily be adapted by changing the cutting distance and lamination tape widths.

The forming of the capillary may comprise cutting out the capillary from at least one spacer. The cutting may comprise a kiss-cut process. In the kiss-cut process, a cutting profile wheel may be used. The spacer, in particular a spacer tape forming after cutting the spacer layer of the test element, may be covered on both sides with one or both of an adhesive and a release liner. The spacer may run through a gap between two contrary rotating wheels, where one wheel is the cutting profile wheel such that an outlined capillary shape may be cut into the spacer. The strip width may be defined by a distance between two cut capillary structures.

The working electrode may comprise at least one reagent, wherein the method may comprise coating a reagent stripe onto at least one carrier layer. The coating may comprise a die coating process. The die coating further may comprise running the reagent stripe through a drier following a coating device.

The supporting tape, e.g., a carrier layer, may be provided, in particular as a polymer foil. On top of the carrier layer, a first electrode carrier layer is laminated. The first electrode carrier layer may be coated with a conductive layer. The first electrode carrier layer may have a smaller width than a width of the supporting tape such that, when laminating the coated electrode carrier layer and the supporting tape, the strip handle may be formed. The spacer layer may be laminated onto the coated first electrode carrier layer. The spacer layer may have a width smaller than the coated first electrode carrier layer. The spacer layer may be laminated onto the coated first electrode carrier layer such that on both edges of the coated first electrode carrier layer a part may be uncovered from the spacer layer, forming an electrode contact zone. The spacer layer may be coated with a conductive material, typically sputtered with a thin silver layer. Onto the spacer layer a conductive adhesive layer may be laminated, such that the first and second electrode contact zones may be uncovered. On top of the conductive adhesive layer, the second electrode carrier layer may be laminated, which may be coated with a thin silver layer, which may coated by a stripe of an Ag/AgCl paste. The stripe may be positioned such that it faces the first electrode reagent layer. Finally, the layer setup may be cut such that the capillary is open at three sides.

Further, the method may comprise creating holes in the test element, e.g., holes for a top dose position, a contact hole, and a vent hole opening. In general, the holes may have an arbitrary shape, e.g., a rectangular shape or a round shape.

In accordance with yet another embodiment of the present disclosure, a system for determining at least one property of a sample is disclosed. The system comprises at least one test element, disclosed in one or more of the embodiments above or disclosed in further detail below. The system further comprises at least one measurement device adapted for performing at least one electrical measurement using the test element. For a description of possible embodiments and definitions of the test element, reference can be made to the above-mentioned test element according to the present disclosure.

As used herein, the term "determining at least one property" refers to detecting at least one analyte in a bodily fluid. However, embodiments wherein other properties may be detected are feasible. As used herein, the term "measurement device" refers to an arbitrary device, typically an electronic device, which may be handled independently from the test element. The measurement device may be adapted to interact with the test element in order to detect the at least one signal produced by one of the first and second electrode and to apply a voltage to the other one of the first and second electrode. The measurement device further may be adapted to derive at least one item of information regarding the presence and/or concentration of the analyte in the body fluid from this detection. Thus, the measurement device may comprise at least one electronic evaluation device interacting with the first and second electrodes, in order to derive the at least one information and/or concentration of the at least one analyte from the at least one signal. Thus, the measurement device may comprise at least one evaluation unit comprising at least one data processing device, such as a microcontroller.

The test element may be inserted into a test element receptacle of the measurement device. As used herein, a test element receptacle may be a mechanical interface adapted to receive the at least one test element. Most typically, the test element receptacle is a test element receptacle adapted to receive precisely one test element at a time. The mechanical interface may be adapted to at least partially receive the test element and to mechanically secure the test element during measurement. The test element receptacle may be configured to contact the first electrode and the second electrode electrically, in particular via contact of the first and second electrode contact zones with at least one connector element of the measurement device, e.g., two pairs of connector pins.

The measurement device may be configured to perform at least one impedance measurement using the first electrode and the second electrode. The measurement device may be further configured to perform at least one amperometric measurement using the first electrode and the second electrode.

The measurement device may be configured to detect both an AC signal and a DC signal. The measurement device may be configured to detect the AC signal and DC signal simultaneously. A parallel determination of both the AC signal and DC signal may be performed by overlapping respective excitation potentials. The measurement device may be configured to detect the AC signal and the DC signal sequentially. The time interval between two measurements may be as short as possible to minimize time-dependent effects. The measurement device may be configured to apply an AC signal to the first electrode and the second electrode and to detect, e.g., continuously, a response. The measurement device may detect a contact time, e.g., a time when the sample may be in contact with the first and second electrode surfaces, by applying the AC signal between the first and the second electrode and measuring the response over time. In case the AC response may exceed a predefined threshold, this may be recognized as "sample dosing detected".

The measurement device is configured to detect the at least one analyte independently of a filling level of the electrochemical cell. By performing a simultaneous AC- and DC-measurement a complete filling of the capillary of the test element may not be necessary. The AC signal may be proportional to the filling level of the capillary. The electro-conductivity G of the electrochemical cell may be proportional to the filling level of the capillary and is defined as:

$$G = x \cdot (l \cdot w)/h,$$

wherein x is a specific conductivity of a sample, l is the filled length of the capillary, w is the width of the capillary and h is the height of the capillary. As described above the height of the electrochemical cell may be defined by a thickness of the spacer layer and of adhesive layers in between the first and second electrode. Further as described above, the term "length of the capillary" refers to a maximum extension of the capillary in one dimension within the test element. In one embodiment, the capillary may extend perpendicular to the elongated test element direction such that in this case the length of the capillary refers to a maximum extension of the capillary perpendicular to the elongated test element direction. In an embodiment, the capillary may extend along the elongated test element direction such that in this case the length of the capillary refers to a maximum extension of the capillary along the elongated test element direction. The term "filled length of the capillary" refers to an amount of the whole capillary length, which is filled by the sample. The term "width" of the capillary refers, in a two dimensional space, to a maximum extension of the capillary in a dimension perpendicular to the length of the capillary.

The amperometric response DC of the electrochemical cell may be proportional to the filling level of the capillary and is defined by the so-called Cottrell function:

$$DC = (l \cdot w) \cdot c \cdot F \cdot z \cdot D^{1/2} \cdot t^{-1/2},$$

wherein F is the Faraday constant, c the initial concentration of the analyte, z the number of transferred electrons, D the diffusion coefficient, and t the measuring time.

Both the electro-conductivity and the amperometric response typically are proportional to the filling level of the capillary such that the relation, e.g., the ratio, of AC and DC measurement value is independent from the filling level. Variations in the filling level and/or effects due to the filling level may be compensated by calibration. Thus, by performing a simultaneous AC- and DC-measurement the test element may be designed without additional dose or fill detect electrodes.

The measurement device may be further configured to electrically monitor a filling process of the capillary. For example, in an embodiment wherein the capillary at least partially may extend along the longitudinal axis of the test element, the measurement device may be configured to electrically monitor when the sample may reach the reagent coating of the working electrode. The reagent coating may comprise at least one redox active substance, which may be oxidized or reduced at the first electrode surface. The measurement device may be configured to apply a DC voltage between the first and the second electrode and to detect a response, in particular a DC response. The sample may start to dissolve the reagent and in case the DC voltage is applied, the DC response, in particular a response signal, may increase. In case the DC response may exceed a predefined threshold, this may be recognized as "analyte detection started". If the time for reaching the reagent coating may exceed a predefined limit, an error message may be generated by the measurement device.

Further, the measurement device may be configured to electrically monitor when the capillary may be filled completely. Thus, after "sample dosing detected" and/or "analyte detection started" was detected, a second AC voltage may be applied to the electrodes and the response may be detected. If the detected response signal may reach a steady state, this may be recognized as filled. If the time for filling may exceed a predefined limit, an error message may be generated by the measurement device. A gradient of the response signal may be measured. If the gradient amounts or exceeds a predefined threshold, this may be recognized as filled. The predefined threshold may be chosen such that a minimum filling level is ensured. The predefined threshold may be chosen with respect to a specific conductivity of a sample. The predefined threshold may be chosen with respect to the sample having the lowest expected specific conductivity. Additional predefined thresholds may be assigned to different values of the gradient of the response signal such that the filling level can be determined and monitored.

The measurement device may be configured to perform at least one initial failsafe measurement before applying the sample of the bodily fluid. The failsafe measurement may comprise at least one electrical measurement using the first electrode and the second electrode. The electrical measurement may be used for deriving at least one electrical measurement value, wherein the failsafe measurement may further comprise comparing the electrical measurement value with at least one threshold value. The failsafe measurement may comprise detecting at least one damage and/or deterioration of the at least one of the first electrode or the second electrode.

In accordance with still another embodiment of the present disclosure, a method for determining at least one property of a sample is disclosed. As outlined above, the term "determining at least one property" refers to detecting at least one analyte in a bodily fluid. With respect to definitions and embodiments reference can be made to definitions and embodiments of a test element, measurement device and a method for producing a test element as disclosed above. In the method, a system for determining at least one property of a sample is used. With respect to definitions and embodiments of the system, reference can be made to the above-mentioned system according to the present disclosure. The method comprises the following steps:

a) Connecting the test element to at least one measurement device;
b) Applying a sample of bodily fluid to a capillary of at least one test element;
c) Determining both an AC signal and a DC signal; and
d) Calibrating measurement results by using the AC and DC signal.

The method steps, as an example, may be performed in the given order. However, a different order is also feasible. Further, one or more or even all of the method steps may be performed in parallel or in a timely overlapping fashion. Further, one or more or even all of the method steps may be performed once or repeatedly. With respect to definitions and embodiments of the test element, capillary and measurement device, reference can be made to definitions and embodiments of the test element, capillary and the measurement system as given above.

In step a) a sample of bodily fluid is applied to a capillary of at least one test element. As used herein, the term "applying" refers to a process of contacting the sample with the test element such that a filling of the capillary is possible and to a process of filling the capillary. The sample of the body fluid may be applicable to one or more of: a side dose position, a top dose position, and a front dose position. The sample may be applied to the test element by a side dose position, e.g., capillary blood from a finger stick may be applied to the side dose position by pressing the finger to the side dose position. The sample of the body fluid may be applied from above through a layer set-up of the test element into the capillary, for example by a transfer device, e.g., a pipette. The sample may be applied to the test element by a front dose position.

As used herein, the term "connecting the test element to at least one measurement device" refers to inserting the test element into a test element receptacle of the measurement device, e.g., a mechanical interface, and electrically contacting the first electrode and the second electrode, in particular via contact of the first and second electrode contact zones with at least one connector element of the measurement device, e.g., two pairs of connector pins.

For a stable amperometric measurement of the at least one property of a sample, e.g., the concentration of glucose in bodily fluid, it may be necessary that the capillary is filled completely before the measurement starts. In principle, filling of a capillary may be determined by additional electrodes such as dose or fill detect electrodes. Renouncing the use of additional electrodes may reduce manufacturing costs and material costs of the test element. The disclosed method permits determining the at least one property of a sample without effects and/or influences of the capillary filling without using additional electrodes. In particular, a complete filling of the capillary may be not necessary. In step c) both an AC signal and a DC signal are determined. As used herein, the term "determining both an AC signal and a DC signal" refers to both of an AC and DC excitation, e.g., a parallel AC and DC excitation, and a detection of both of AC and DC response signals. The AC response signal may be or may be proportional to the electro conductivity of the electrochemical cell. The AC signal and the DC signal may be determined simultaneously or sequentially. The determination of the AC and DC signal may be performed by overlapping excitation potentials.

In step d) the measurement results are calibrated by using the AC and DC signal. As used herein, the term "calibration" refers to reducing, typically eliminating, an influence and/or an impact of the filling level of the capillary to the AC response signal and/or DC response signal. Both the AC signal and the DC signal may be proportional to the filling level of the capillary such that effects due to a filling of the capillary are compensated. The AC response signal may be or may be proportional to the electro-conductivity of the electrochemical cell. The electro-conductivity G of the electrochemical cell may be proportional to the filling level of the capillary and is defined as:

$$G = x \cdot (l \cdot w)/h,$$

wherein x is a specific conductivity of a sample, l is the filled length of the capillary, w is the width of the capillary, and h is the height of the capillary. The DC response signal may be or may be proportional to the amperometric response DC of the electrochemical cell, which is defined by the so-called Cottrell function:

$$DC = (l \cdot w) \cdot c \cdot F \cdot z \cdot D^{1/2} \cdot t^{-1/2},$$

wherein F is the Faraday constant, c the initial concentration of the analyte, z the number of transferred electrons, D the diffusion coefficient, and t the measuring time. Thus, both of the AC response signal and the DC response signal may be proportional to the filled length of the capillary. By measuring AC and DC signal simultaneously, effects due to varying filling level may be compensated. The determined values of electro-conductivity G and the amperometric response DC may be combined. Effects due to varying filling levels of the capillary may be compensation by a suitable calibration. For example, a ratio of the electro-conductivity G and the amperometric response may be used. Thus, the fraction may be reduced by the filled length of the capillary. Consequently, the method, specifically method step d), may imply forming a ratio, such as a ratio of G and the DC response signal and/or a ratio of the AC response signal and the DC response signal, wherein the ratio is independent from the filling length l, i.e., independent from the filling level of the electrochemical cell, e.g., under constant temperature conditions and other measurement conditions.

The method may further comprise determining a contact time, wherein an AC signal may be applied between at least one first electrode and at least one second electrode of the test element. A response over time may be measured, for example an AC response signal may be detected. As used herein, the term "contact time" refers to a time when the sample may be in contact with the first and second electrode surfaces. The AC response may be compared to a predefined threshold. In case the AC response may exceed a predefined threshold, this may be recognized as "sample dosing detected".

The method may further comprise determining a filling level of the capillary, wherein an AC signal may be applied between the at least one first electrode and the at least one second electrode of the test element, and wherein a response signal over time may be measured, wherein the response may be compared to at least one predefined threshold. As used herein, the term "determining a filling level of the capillary" may generally refer to an arbitrary process of generating at least one item of information on a filling of the capillary. Thus, the at least one item of information may, as an example, comprise an item of information on whether the filling level is above or below at least one predetermined or determinable threshold, as will be explained in further detail below. Additionally or alternatively, however, one or more other items of information on the filling may be determined.

For example, after "sample dosing detected" and/or "analyte detection started" was detected, a second AC voltage may be applied to the electrodes. If the detected response signal may reach a steady state, this may be recognized as filled. If the time for filling may exceed a predefined limit, an error message may be generated by the measurement device. A gradient of the response signal may be measured. If the gradient amounts or exceeds the predefined threshold, this may be recognized as filled. The predefined threshold may be chosen such that a minimum filling level is ensured. The predefined threshold may be chosen with respect to a specific conductivity of a sample. The predefined threshold may be chosen with respect to the sample having the lowest expected specific conductivity. Additional predefined thresholds may be assigned to different values of the gradient of the response signal such that the filling level can be determined and monitored.

The method may further comprise monitoring a filling process of the capillary, wherein a DC voltage may be applied between the first electrode and the second electrode. A DC response may be detected. The DC response may be compared to a predefined limit. When the sample may reach the reagent coating of the working electrode, the reagent coating, which may comprise at least one redox active substance, may be oxidized or reduced at the first electrode surface. A DC voltage may be applied between the first and the second electrode and the response, in particular a DC response, may be detected. The sample may start to dissolve the reagent and in case the DC voltage is applied, the DC response, in particular a response signal, may increase. In case the DC response may exceed a predefined threshold, this may be recognized as "analyte detection started". If the time for reaching the reagent coating may exceed a predefined limit, an error message may be generated by the measurement device.

Summarizing the findings of the present disclosure, the following embodiments are typical:

Embodiment 1

A test element for electrochemically detecting at least one analyte in a bodily fluid, wherein the test element comprises at least one first electrode and at least one second electrode, wherein the first electrode is designed as a working electrode and the second electrode is designed as a counter electrode, wherein the test element comprises at least one capillary capable of receiving a sample of the body fluid, wherein the first electrode and the second electrode are arranged on opposing sides of the capillary, wherein the first electrode and the second electrode and the capillary in between the first electrode and the second electrode form an electrochemical cell, wherein the test element is configured to detect the at least one analyte independently of a filling level of the electrochemical cell, wherein the first electrode and the second electrode are arranged such that during a capillary filling the first electrode and the second electrode are wetted simultaneously and at an equal rate.

Embodiment 2

The test element according to the preceding embodiment, wherein the first electrode extends over a full length of the capillary.

Embodiment 3

The test element according to any one of the preceding embodiments, wherein the second electrode extends over a full length of the capillary.

Embodiment 4

The test element according to any one of the preceding embodiments, wherein an increment of a wetted surface area $dA1$ of the first electrode per increment $dV$ of a filled volume of the capillary at all times equals an increment of a wetted surface area $dA2$ of the second electrode.

Embodiment 5

The test element according to any one of the preceding embodiments, wherein at least one wall of the test element located outside the capillary but next to the opening for receiving the sample of the body fluid is at least partially covered by at least one hydrophobic coating.

Embodiment 6

The test element according to the preceding embodiment, wherein the electrochemical cell extends over the full length of the capillary.

Embodiment 7

The test element according to any one of the preceding embodiments, wherein the first electrode and the second electrode are made of a non-corrosive and non-passivating material.

Embodiment 8

The test element according to any one of the preceding embodiments, wherein a surface area of the first electrode and a surface area of the second electrode forming the electrochemical cell have the same dimension.

Embodiment 9

The test element according to any one of the preceding embodiments, wherein the first electrode comprises at least one first electrode conductive layer and at least one reagent coating in contact with the first electrode conductive layer.

Embodiment 10

The test element according to the preceding embodiment, wherein the first electrode conductive layer comprises at least one of: a metal layer, typically a noble metal layer selected from the group consisting of palladium, platinum, silver or gold; a conductive carbon layer, in particular a carbon paste layer.

Embodiment 11

The test element according to any one of the two preceding embodiments, wherein the first electrode conductive layer is disposed on a first electrode carrier layer, typically a first electrode carrier foil.

Embodiment 12

The test element according to the preceding embodiment, wherein the first electrode conductive layer extends from a first longitudinal edge of the first electrode carrier layer to a second longitudinal edge of the first electrode carrier layer.

Embodiment 13

The test element according to the preceding embodiment, wherein the first electrode conductive layer fully covers the first electrode carrier layer.

Embodiment 14

The test element according to any one of the five preceding embodiments, wherein the reagent coating comprises at least one reagent stripe coated onto the first electrode conductive layer.

Embodiment 15

The test element according to any one of the preceding embodiments, wherein the second electrode comprises at least one second electrode conductive layer.

Embodiment 16

The test element according to the preceding embodiment, wherein the second electrode conductive layer comprises at least one of: a metal layer, typically a noble metal layer selected from the group consisting of palladium, platinum, silver or gold; a conductive carbon layer, in particular a carbon paste layer.

Embodiment 17

The test element according to any one of the two preceding embodiments, wherein the second electrode further comprises Ag/AgCl, in particular an Ag/AgCl paste.

Embodiment 18

The test element according to any one of the three preceding embodiments, wherein the second electrode conductive layer is disposed on a second electrode carrier layer, typically a second electrode carrier foil.

Embodiment 19

Test element according to the preceding embodiment, wherein the second electrode conductive layer extends from a first longitudinal edge of the second electrode carrier layer to a second longitudinal edge of the second electrode carrier layer.

Embodiment 20

The test element according to the preceding embodiment, wherein the second electrode conductive layer fully covers the second electrode carrier layer.

Embodiment 21

The test element according to any one of the preceding embodiments, wherein the test element is a test strip.

Embodiment 22

The test element according to any one of the preceding embodiments, wherein the capillary is open at three sides.

Embodiment 23

The test element according to any one of the preceding embodiments, wherein a sample of bodily fluid is applicable to one or more of: a side dose position, a top dose position, a front dose position.

Embodiment 24

The test element according to any one of the preceding embodiments, wherein the test element comprises a top dose position and further comprises a through hole extending through a cover foil into the capillary, in particular extending through a cover foil into the capillary in a way that the condition that the increment of a wetted surface area $dA1$ of the first electrode per increment $dV$ of a filled volume of the capillary at all times equals an increment of a wetted surface area $dA2$ of the second electrode is still met.

Embodiment 25

The test element according to any one of the preceding embodiments, wherein the test element has an elongated shape extending along a longitudinal axis, wherein the capillary at least partially extends along the longitudinal axis of the test element.

Embodiment 26

The test element according to any one of the preceding embodiments, wherein the test element has an elongated shape extending along a longitudinal axis, wherein the capillary at least partially extends perpendicular to the longitudinal axis.

Embodiment 27

The test element according to the preceding embodiment, wherein the capillary extends from a first opening at a first longitudinal edge of the test element to a second opening at a second longitudinal edge of the test element.

Embodiment 28

The test element according to the preceding embodiment, wherein the test element comprises a side dose position located at one or both of the first opening or the second opening.

Embodiment 29

The test element according to any one of the three preceding embodiments, wherein the capillary has an open side at a front face of the test element.

Embodiment 30

The test element according to the preceding embodiment, wherein the test element has a front dose position located at the front face of the test element.

Embodiment 31

The test element according to any one of the preceding embodiments, wherein the capillary comprises a vent hole opening.

Embodiment 32

The test element according to any one of the preceding embodiments, wherein the test element comprises a strip handle.

Embodiment 33

The test element according to the preceding embodiment, wherein the test element comprises a layer setup disposed on top of at least one carrier element, wherein the carrier element, in a longitudinal direction of the test element, protrudes from the layer setup, thereby forming the strip handle.

Embodiment 34

The test element according to any one of the preceding embodiments, wherein the test element comprises a first electrode contact zone and a second electrode contact zone configured to contact the first electrode and the second electrode with a further device, in particular a meter.

Embodiment 35

The test element according to the preceding embodiment, wherein the first electrode contact zone and the second electrode contact zone are configured to be electrically contacted from the same side of the test element.

Embodiment 36

The test element according to the preceding embodiment, wherein the first electrode contact zone and the second electrode contact zone are arranged in different layers of a layer setup of the test element, wherein one of the first electrode contact zone and the second electrode contact zone protrudes over the other one of the first electrode contact zone and the second electrode contact zone.

Embodiment 37

The test element according to the preceding embodiment, wherein the first electrode contact zone and the second electrode contact zone form different steps of a staircase configuration of the layer setup.

Embodiment 38

The test element according to any one of the four preceding embodiments, wherein the first electrode contact zone and the second electrode contact zone are configured to be electrically contacted from opposing sides of the test element.

Embodiment 39

The test element according to the preceding embodiment, wherein a punched hole through a cover foil and a spacer layer is configured as the second electrode contact zone, in particular a contact hole.

Embodiment 40

The test element according to any one of the preceding embodiments, wherein the test element comprises at least one carrier element.

Embodiment 41

The test element according to any one of the preceding embodiments, wherein the test element comprises a layer setup, wherein the first electrode comprises at least one first electrode conductive layer disposed on at least one first electrode carrier layer, wherein the second electrode comprises at least one second electrode conductive layer disposed on at least one second electrode carrier layer.

Embodiment 42

The test element according to the preceding embodiment, wherein the layer setup is arranged such that the first electrode conductive layer faces the second electrode conductive layer, with the capillary in between.

Embodiment 43

The test element according to any one of the two preceding embodiments, wherein at least one spacer layer is disposed in between the first electrode conductive layer and the second electrode conductive layer.

Embodiment 44

The test element according to any one of the preceding embodiments, wherein one or both of the first electrode or the second electrode are electrically contacted by at least one electrically conductive turnover element, wherein the first or second electrode, respectively, are oriented to face a first direction, wherein the electrically conductive turnover element is contactable from a second direction, the second direction being an opposite direction of the first direction.

Embodiment 45

The test element according to the preceding embodiment, wherein the electrically conductive turnover element comprises at least one of an electrically conductive layer or an electrically conductive foil having a first section and a second section, the first section electrically contacting the first or second electrode, respectively, and the second section being electrically contactable.

Embodiment 46

The test element according to the preceding embodiment, wherein the electrically conductive turnover element is partially covered by at least one layer comprising the first or second electrode, respectively, wherein the second section is located in an uncovered region.

Embodiment 47

The test element according to any one of the two preceding embodiments, wherein the electrically conductive turn-over element is laminated to the first or second electrode, respectively.

Embodiment 48

A method for producing a test element according to any one of the preceding embodiments, the method comprising at least one step of forming a layer setup, wherein the first electrode, the second electrode and the capillary are formed such that the first electrode and the second electrode are arranged on opposing sides of the capillary.

Embodiment 49

The method according to the preceding embodiment, wherein the test element is a test strip.

Embodiment 50

The method according to any one of the preceding method embodiments, wherein the test element is produced in a continuous process, typically in a reel-to-reel process.

Embodiment 51

The method according to any one of the preceding method embodiments, wherein the step of forming the layer setup comprises at least one lamination step, wherein, in the lamination step, at least two layers are combined by a lamination process.

Embodiment 52

The method according to the preceding embodiment, wherein the lamination step comprises a lamination of at least two tapes.

Embodiment 53

The method according to any one of the preceding method embodiments, the method further comprises cutting the layer setup into test strips.

Embodiment 54

The method according to the preceding embodiment, wherein the layer setup is a tape-shaped layer setup, wherein a width of the tape-shaped layer setup defines a length of the test strips.

Embodiment 55

The method according any one of the preceding method embodiments, wherein the forming of the capillary comprises cutting out the capillary from at least one spacer layer.

Embodiment 56

The method according to the preceding embodiment, wherein the cutting comprises a kiss-cut process.

Embodiment 57

The method according to any one of the five preceding embodiments, wherein the working electrode comprises at least one reagent, wherein the method comprises coating a reagent stripe onto at least one carrier layer.

Embodiment 58

The method according to the preceding embodiment, wherein the coating comprises a die coating process.

Embodiment 59

The method according to the preceding embodiment, wherein the die coating further comprises running the reagent stripe through a drier following a coating device.

Embodiment 60

A system for determining at least one property of a sample, the system comprising at least one test element according to any one of the preceding embodiments referring to a test element, the system further comprising at least one measurement device adapted for performing at least one electrical measurement using the test element.

Embodiment 61

The system according to the preceding embodiment, wherein the test element comprises at least one first electrode and at least one second electrode, wherein the first electrode is designed as a working electrode and the second electrode is designed as a counter electrode, wherein the test element comprises at least one capillary capable of receiving a sample of the body fluid, wherein the first electrode and the second electrode are arranged on opposing sides of the capillary, wherein the first electrode and the second electrode and the capillary in between the first electrode and the second electrode form an electrochemical cell, wherein the test element is configured to detect the at least one analyte independently of a filling level of the electrochemical cell, wherein the first electrode and the second electrode are arranged such that during a capillary filling the first electrode and the second electrode are wetted simultaneously and at an equal rate, the system further comprising at least one measurement device adapted for performing at least one electrical measurement using the test element, wherein the measurement device is configured to detect both an AC signal and a DC signal, wherein the measurement device is configured to detect the at least one analyte independently of a filling level of the electrochemical cell.

Embodiment 62

The system according to any one of the preceding embodiments referring to a system, wherein the measurement device is configured to perform at least one impedance measurement using the first electrode and the second electrode.

Embodiment 63

The system according to any one of the two preceding embodiments, wherein the measurement device further is configured to perform at least one amperometric measurement using the first electrode and the second electrode.

Embodiment 64

The system according to any one of the preceding embodiments referring to a system, wherein the measurement device is configured to detect both an AC signal and a DC signal.

Embodiment 65

The system according to the preceding embodiment, wherein the measurement device is configured to detect the AC signal and the DC signal sequentially.

Embodiment 66

The system according to any one of the two preceding embodiments, wherein the measurement device is configured to apply an AC signal to the first electrode and the second electrode and to detect a response.

Embodiment 67

The system according to any one of the preceding embodiments referring to a system, wherein the measurement device is further configured to electrically monitor a filling process of the capillary.

Embodiment 68

The system according to any one of the preceding embodiments referring to a system, wherein the measurement device is configured to perform at least one initial failsafe measurement before applying the sample of bodily fluid.

Embodiment 69

The system according to the preceding embodiment, wherein the failsafe measurement comprises at least one electrical measurement using the first electrode and the second electrode.

Embodiment 70

The system according to the preceding embodiment, wherein the electrical measurement is used for deriving at least one electrical measurement value, wherein the failsafe measurement further comprises comparing the electrical measurement value with at least one threshold value.

Embodiment 71

The system according to any one of the three preceding embodiments, wherein the failsafe measurement comprises detecting at least one damage and/or deterioration of at least one of the first electrode or the second electrode.

Embodiment 72

A method for determining at least one property of a sample, wherein a system according to any one of the preceding embodiments referring to a system is used, wherein the method comprises the following steps:

a) Connecting the test element to at least one measurement device;
b) Applying a sample of bodily fluid to a capillary of at least one test element;
c) Determining both an AC signal and a DC signal;
d) Calibrating measurement results by using the AC and DC signal.

Embodiment 73

The method according to the preceding embodiment, wherein the AC signal and the DC signal are determined simultaneously or sequentially.

Embodiment 74

The method according to any one of the preceding embodiments referring to a method for determining at least one property of a sample, wherein the determination of the AC and DC signal is performed by overlapping excitation potentials.

Embodiment 75

The method according to any one of the preceding embodiments referring to a method for determining at least one property of a sample, wherein both the AC signal and the DC signal are proportional to the filling level of the capillary such that effects due to a filling of the capillary are compensated.

Embodiment 76

The method according to any one of the preceding embodiments referring to a method for determining at least one property of a sample, wherein the method further comprises determining a contact time, wherein an AC signal is applied between at least one first electrode and at least one second electrode of the test element, wherein a response over time is measured, wherein the response is compared to a predefined threshold.

Embodiment 77

The method according to any one of the preceding embodiments referring to a method for determining at least one property of a sample, wherein the method further comprises determining a filling level of the capillary, wherein an AC signal is applied between the at least one first electrode and the at least one second electrode of the test element, wherein a response signal over time is measured, wherein the response is compared to at least one predefined threshold, wherein the predetermined threshold is chosen such that a minimum filling level is ensured.

Embodiment 78

The method according to the preceding embodiment, wherein the predefined threshold is chosen with respect to a specific conductivity of a sample.

Embodiment 79

The method according to any one of the preceding embodiments referring to a method for determining at least one property of a sample, wherein the method further comprises monitoring a filling process of the capillary, wherein a DC voltage is applied between the first electrode and the second electrode, wherein a DC response is detected, wherein the DC response is compared to a predefined limit.

Figure 2:
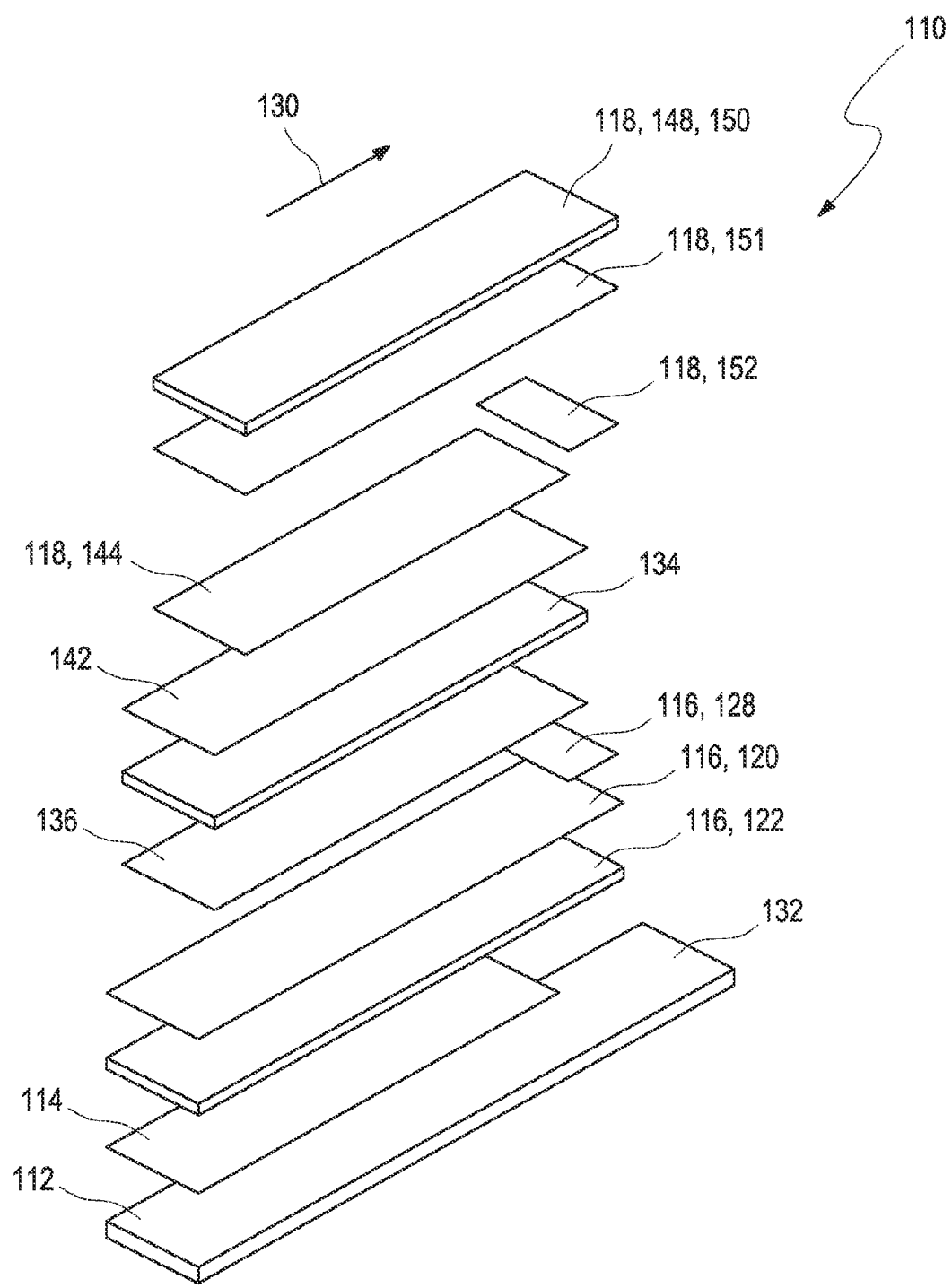
FIG. 2 shows an exploded drawing of the test element according to the present disclosure.

In FIGS. 1 to 3 a first embodiment of a test element 110 according to the present disclosure is shown. FIG. 1 shows an exemplary arrangement of different layers of a tape-shaped layer setup of the test element 110, in particular before cutting the layer setup into individual test elements 110, whereas in FIG. 2 an exploded drawing of one individual test element 110 is depicted. The test element 110 is adapted for electrochemically detecting at least one analyte in a bodily fluid. The at least one analyte may be a component or compound present in a body fluid and the concentration of which may be of interest for a user. As an example, the at least one analyte may be selected from the group consisting of glucose, cholesterol, triglycerides, and lactate. Additionally or alternatively, however, other types of analytes may be used and/or any combination of analytes may be determined. The body fluid may be whole blood, such as a sample of capillary blood taken from a finger stick.

The test element 110 may comprise at least one carrier element 112, such as at least one carrier foil. For example, the carrier element 112 may be a polymer foil that may be configured to provide stability for the test element 110, such that it can be handled by a user, typically without deflections and/or fractions. An adhesive layer 114 may be laminated onto the carrier element 112.

The test element 110 comprises at least one first electrode 116 and at least one second electrode 118. The first electrode 116 is designed as a working electrode and the second electrode 118 is designed as a counter electrode. The first electrode 116 and the second electrode 118 may be made of a non-corrosive and non-passivating material. In the first embodiment shown in FIGS. 1 to 3, the first electrode 116 may be arranged on top of the adhesive layer 114. The first electrode 116 may comprise at least one first electrode conductive layer 120. The first electrode conductive layer 120 may comprise at least one of: a metal layer, typically a noble metal layer selected from the group consisting of palladium, platinum, silver and gold; a conductive carbon layer, in particular a carbon paste layer. The first electrode conductive layer 120 may be disposed on a first electrode carrier layer 122, such as a first electrode carrier foil. For example, the first electrode carrier layer 122 may be coated with a conductive carbon paste or with a noble metal layer, e.g., gold, palladium or platinum. The first electrode conductive layer 120 may extend from a first longitudinal edge 124 of the first electrode carrier layer 122 to a second longitudinal edge 126 of the first electrode carrier layer 122. The first electrode conductive layer 120 may fully cover the first electrode carrier layer 122. The first electrode 116 may comprise at least one reagent coating 128 in contact with the first electrode conductive layer 120. The reagent coating 128 may comprise at least one reagent stripe coated onto the first electrode conductive layer 120. For example, the reagent stripe may be coated by a die coating process by a coating device and may be dried by running through a drier following the coating device.

The test element 110 may comprise a strip handle 132. The test element 110 shown may comprise a layer setup disposed on top of the carrier element 112. The carrier element 112, along a longitudinal axis 130 of the test element 110, may protrude from the layer setup, thereby forming the strip handle 132. Therefore, the first electrode carrier layer 122 may have a smaller width than the width of the carrier element 112. Additionally or alternatively, embodiments are feasible, wherein the test element 110 may be configured without a protruding carrier element 112 as strip handle 132. In this embodiment, a length of the test element 110 may be such that a user may grip between a dosing side and a further device in which the test element 110 may be inserted.

On top of the first electrode 116, a spacer layer 134, such as a polymer foil, may be laminated. In between the first electrode 116 and the spacer layer 134, an adhesive layer 136 may be positioned. The test element 110 may comprise a first electrode contact zone 138 configured to contact the first electrode 116 with a further device. The spacer layer 134 may have a smaller width than the width of the first electrode carrier layer 122. The spacer layer 134 may be arranged such that parts of the first electrode carrier layer 122 may be uncovered by the spacer layer 134, in particular such that the first electrode carrier layer 122 may protrude from the spacer layer 134 on both sides. Thus, on one protruding side the first electrode contact zone 138 may be created and on the other side a measurement zone 140 may be created. The spacer layer 134 may be coated with a conductive material layer 142, e.g., the spacer layer 134 may be sputtered with a thin silver layer. Further, on top of the conductive material layer 142 a conductive adhesive layer 144, such as a silver particle based adhesive layer, may be laminated. The test element 110 may comprise a second electrode contact zone 146 configured to contact the second electrode 118 with the further device. The conductive adhesive layer 144 may have a smaller width that the width of the spacer layer 134. The conductive adhesive layer 144 may be positioned such that a part of the conductive material layer 144 pointing to the first electrode contact zone 138 may be uncovered by the conductive adhesive layer 144, in particular such that the conductive material layer 144 may protrude from the conductive adhesive 144 on one side. Thus, the second electrode contact zone 146 may be created.

The second electrode 118 may be arranged on top of the conductive adhesive layer 144. The first electrode 116 and the second electrode 118 may have the same dimension. The second electrode 118 may comprise at least one second electrode conductive layer 148. The second electrode conductive layer 148 may comprise at least one of: a metal layer, typically a noble metal layer selected from the group consisting of palladium, platinum, silver or gold; a conductive carbon layer, in particular a carbon paste layer. The second electrode conductive layer 148 may be disposed on a second electrode carrier layer 150, such as a second electrode carrier foil. For example, the second electrode carrier layer 150 may be metallized on one side facing after a lamination step the spacer layer 134, typically by a silver layer. For example, the second electrode carrier layer 150 may be coated by a conductive adhesive layer 151, e.g., based on silver particles. The second electrode 118 may further comprise Ag/AgCl, in particular an Ag/AgCl paste. For example, in this first embodiment, the metallized side of the electrode carrier layer 150 may be coated with a strip of an Ag/AgCl paste 152. The second electrode conductive layer 148 may extend from a first longitudinal edge 154 of the second electrode carrier layer 150 to a second longitudinal edge 156 of the second electrode carrier layer 150. The second electrode conductive layer 148 may fully cover the second electrode carrier layer 150. The strip of Ag/AgCl paste may be positioned such that after the lamination step, the second electrode carrier layer 150 may face the reagent coating 128. In an alternative embodiment, instead of the silver layer coating, the electrode carrier layer 150 may be coated completely by an Ag/AgCl paste. In a further alternative embodiment, a redox electrode can be used as the counter electrode. Such a redox electrode comprises a conductive layer, e.g., a conductive carbon layer, coated with a reagent layer comprising an reducible substance, e.g., an organic redox mediator. Arrows 158 shown in FIG. 1 indicate that the depicted laminated second electrode 118 may be turned onto the conductive adhesive 144.

The test element 110 comprises at least one capillary 160 capable of receiving a sample of the body fluid. The first electrode 116 and the second electrode 118 are arranged on opposing sides of the capillary 160. The first electrode 116 and the second electrode 118 may be arranged as opposing electrodes, such that a surface of the first electrode 116 faces a surface of the second electrode 118. The first electrode 116 and the second electrode 118 may be aligned in parallel. The first electrode 116 and the second electrode 118 and the capillary 160 in between the first electrode 116 and the second electrode 118 may form an electrochemical cell. By laminating the second electrode 118 onto the conductive adhesive 144, the electrochemical cell may be created. The electrochemical cell may extend over the full length of the capillary 160. A height of the electrochemical cell may be defined by a thickness of the spacer layer 134 and adhesive layers in between the first electrode 116 and the second electrode 118. To avoid a change of the height of the electrochemical cell during a measurement, e.g., when the strip handle 132 is touched by a user such that the test element 110 is bent, the adhesive layer 114 may be designed such that a region defined by a position of the electrochemical cell may be not covered by the adhesive layer 114 such that a gap 161 between the carrier element 112 and the first electrode 116 may be formed, see FIG. 3B. Thus, in case a user may inadvertently bend the test element 110, a distance between the first and the second electrode surfaces may be unaffected. The first electrode 116 may extend over a full length of the capillary 160. The second electrode 118 may extend over a full length of the capillary 160. The first electrode 116 and the second electrode 118 are arranged such that during a capillary filling the first electrode 116 and the second electrode 118 are wetted simultaneously and at an equal rate. An increment of a wetted surface area dA1 of the first electrode 116 per increment dV of a filled volume of the capillary 160 at all times may equal an increment of a wetted surface area dA2 of the second electrode 118. Thus, the test element 110 may be configured to detect the at least one analyte independently of a filling level of the electrochemical cell.

The test element 110 may be produced in a method according to the present disclosure. The method comprises at least one step of forming a layer setup, e.g., as the layer setup shown in FIGS. 1 to 3. The test element 110 may be produced in a continuous process, typically in a reel-to-reel process. The step of forming the layer setup may comprise at least one lamination step, wherein, in the lamination step, at least two layers are combined by a lamination process. The lamination step may comprise a lamination of at least two tapes. The method further may comprise cutting the layer setup into individual test elements 110 such as test strips. The cutting and cutting lines 162 are indicated in FIG. 1. The layer setup may be a tape-shaped layer setup, wherein a width of the tape-shaped layer setup may define a length of the test strip. The resulting test element 110 may have an elongated shape extending along the longitudinal axis 130, wherein the capillary 160 may at least partially extend perpendicular to the longitudinal axis 130 of the test element 110. By cutting the layer setup into individual test elements 110, the capillary 160 may be open at three sides. According to the present disclosure, the sample of body fluid may be applicable to one or more of: a side dose position, a top dose position, a front dose position. In the first embodiment of the test element 110, the capillary 160 may have two side dose positions 164 and one front dose position 166, best seen in FIG. 3A. The capillary 160 may extend from a first opening at a first longitudinal edge of the test element 110, e.g., a first side dose position 164, to a second opening at a second longitudinal edge of the test element 110, e.g., a second side dose position 164. The side dose positions may be an ideal application position for capillary blood from a finger stick. The test element 110 may have an open side at a front face 168 of the test element 110. The test element 110 may have one front dose position 166 located at the front face 168 of the test element 110. In front of the capillary 160, such as in direction of the strip handle 132, the carrier element 112 may be coated with a hydrophobic coating. FIG. 3B shows a cross-section of the test element 110.

As outlined above, the test element 110 may comprise the first electrode contact zone 138 and the second electrode contact zone 146 configured to contact the first electrode 116 and the second electrode 118 with a further device. In FIG. 3A, a system according to the present disclosure is shown. The system 170 comprises at least one test element 110. The system further comprises at least one measurement device 172 adapted for performing at least one electrical measurement using the test element 110. The first electrode contact zone 138 and the second electrode contact zone 146 may be configured to be electrically contacted from the same side 174 of the test element 110. The first electrode contact zone 138 and the second electrode contact zone 146 may be arranged in different layers of a layer setup of the test element 110, wherein one of the first electrode contact zone 138 and the second electrode contact zone 146 may protrude over the other one of the first electrode contact zone 138 and the second electrode contact zone 146. The first electrode contact zone 138 and the second electrode contact zone 146 may form different steps of a staircase configuration of the layer setup. However, as the first electrode 116 and the second electrode 118 may be configured as opposing electrodes, to allow an electrically contact from the same side 174 of the test element 110, the first electrode 116 or the second electrode 118 may be electrically contacted by at least one electrically conductive turnover element 176. The first electrode 116 or the second electrode 118, respectively, may be oriented to face a first direction, wherein the electrically conductive turnover element 176 may be contactable from a second direction, the second direction being an opposite direction of the first direction. The electrically conductive turnover element 176 may comprise at least one of an electrically conductive layer or an electrically conductive foil having a first section and a second section, the first section electrically contacting the first electrode 116 or the second electrode 118, respectively, and the second section being electrically contactable. The electrically conductive turnover element 176 may be partially covered by at least one layer comprising the first electrode 116 or the second electrode 118, respectively, wherein the second section may be located in an uncovered region. The electrically conductive turnover element 176 may be laminated to the first electrode 116 or second electrode 118, respectively. For example, the conductive material layer 142 and the conductive adhesive layer 144 may be adapted as turnover element 176. The first electrode contact zone 138 and second electrode contact zone 146 may be hit upon by at least one connector 178 of the measurement device 172, e.g., meter connector pins. The measurement device 172 may have two pairs of connectors 178, one pair for each of the first electrode 116 and the second electrode 118. One connector 178 of each connector pair may be configured to support a current flow through the test element 110. The other connector 178 may be used to detect a voltage. Such a configuration, also called 4-wire-technique, may allow an electronic controller of the measurement device 172 to compensate voltage drop induced by parasitic transfer resistances at connection spots of the first electrode contact zones 138 and second electrode contact zones 146 and the connectors 178.

The measurement device 172 may be configured to perform at least one impedance measurement using the first electrode 116 and the second electrode 118. The measurement device 172 may be configured to apply an AC signal to the first electrode 116 and the second electrode 118 and to detect a response. The measurement device 172 may be configured to perform at least one initial failsafe measurement before applying the sample of bodily fluid. The failsafe measurement may comprise at least one electrical measurement using the first electrode 116 and the second electrode 118. The electrical measurement may be used for deriving at least one electrical measurement value, wherein the failsafe measurement further may comprise comparing the electrical measurement value with at least one threshold value. The failsafe measurement may comprise detecting at least one damage and/or deterioration of at least one of the first electrode 116 or the second electrode 118. The at least one damage and/or deterioration, such as a scratch on a conductive surface of the first electrode 116 and/or the second electrode 118, may result in interrupting the conductive surface before or within the electrochemical cell.

Figure 4:
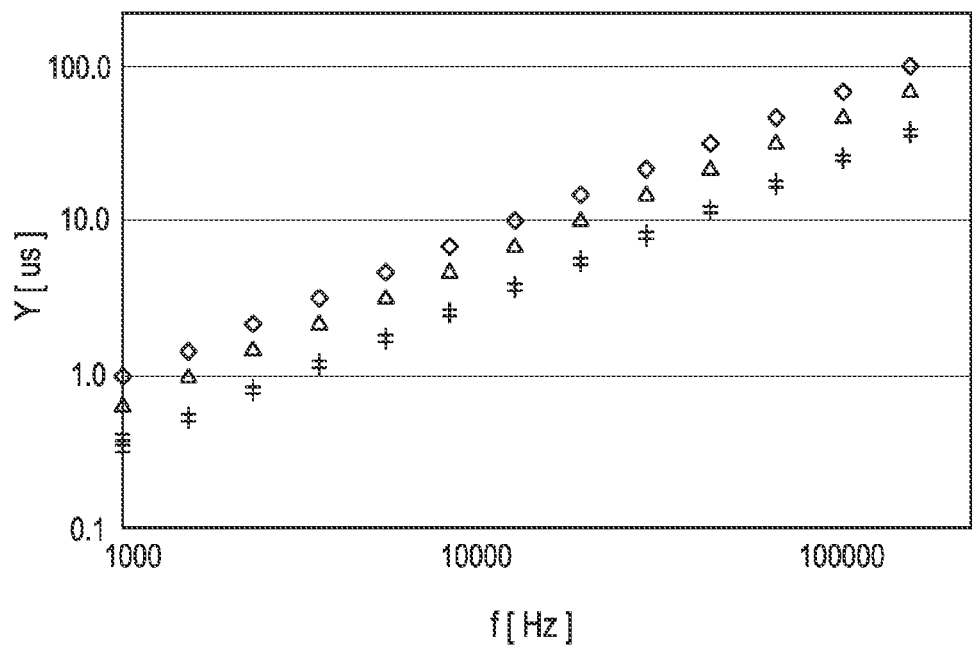
FIG. 4A shows a histogram of an impedance measurement of a failsafe measurement.
FIG. 4B shows a histogram used for monitoring a filling process.
Figure 4:
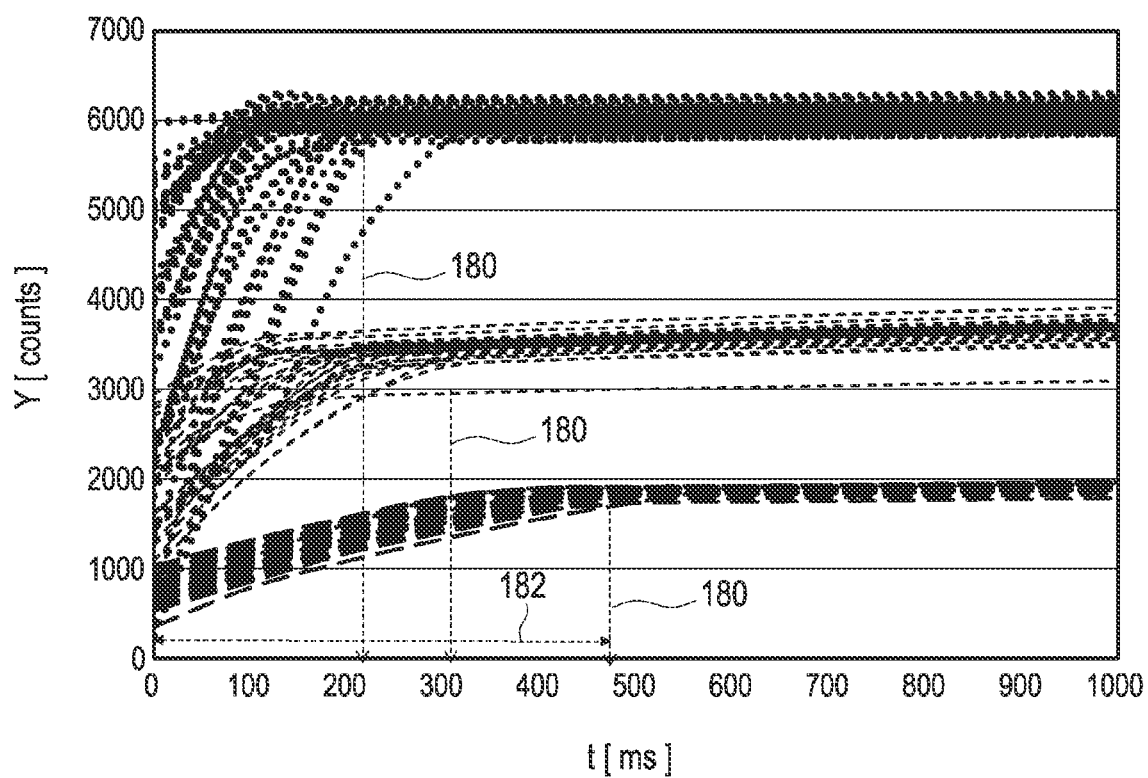

FIG. 4A shows a histogram of an impedance measurement of a failsafe measurement. For this measurement, an AC signal may be applied to the first electrode 116 and the second electrode 118, in particular a 10 mV rms (root mean square) AC voltage, and the complex impedance may be measured. The histogram shows the resulting admittance Y at different frequencies f measured between the first electrode 116 and the second electrode 118. Measurement results of five test elements 110 with scratches applied to on one of the first electrode conductive layer 120 close to the first electrode contact zone 138 or the second electrode conductive layer 148 close to the second electrode contact zone 146, indicated as crosses, are compared to measurement results of five test elements 110 with scratches applied to on one of the first electrode conductive layer 120 close to the electrochemical cell or the second electrode conductive layer 148 close to the electrochemical cell, indicated as triangles, and to measurement results of test elements 110 with no scratches, indicated as rhombus. The measurement results show a shift of the admittance. Thus, by using a phase information and an admittance information at different frequencies, it may be possible to separate the effect of scratches from otherwise changed conductivities, for example caused by a variable thickness of the first electrode and/or second electrode conductive layers 120, 148.

The measurement device 172 may further be configured to perform at least one amperometric measurement using the first electrode 116 and the second electrode 118. The measurement device 172 may be configured to detect both an AC signal and a DC signal. The measurement device 172 may be configured to detect the AC signal and the DC signal sequentially. The measurement device 172 may be further configured to electrically monitor a filling process of the capillary 160. An AC signal may be applied to the first electrode 116 and the second electrode 118. After it was detected that the sample of body fluid touches first the first electrode 116 and the second electrode 118, the AC response may further increase, because the wetted surface area dA1 of the first electrode 116 and the wetted surface area dA2 of the second electrode 118 may increase continuously. If the response signal may reach a certain threshold, this time may be detected as "Filling complete" and a test sequence to carry out an analytical measurement of the at least one analyte in the body fluid may start. The term to reach a constant value may refer to a response gradient falls under a predefined threshold. In case the measurement device 172 may not detect the response signal reaching a constant value within a predefined time, an error message may be generated by the measurement device 172 and/or the measurement may be stopped. FIG. 4B shows a histogram used for monitoring a filling process for three different blood samples, adjusted to different hematocrit levels of 70% (long dashed set of curves), 43% (short dashed set of curves), and 0% (dotted set of curves). The AC signal was integrated and is depicted as admittance Y versus a filling time t after detecting that the sample of body fluid touches first the first electrode 116 and the second electrode 118. The vertical dashed arrows 180 indicate the time where the constant value is reached. The horizontal arrow 182 indicates a period of time to reach the constant value.

A second embodiment of the test element 110 is shown in FIGS. 5A to 7. For a detailed description of the layer setup of the test element 110, reference can be made to the description of the first embodiment above or a description of further embodiments given below. In the second embodiment of the test element 110, the capillary 160 may have two side dose positions 164 and one top dose position 184, see, e.g., FIGS. 5A and 5B. The capillary 160 may extend from a first opening at a first longitudinal edge of the test element 110, e.g., the first side dose position 164, to a second opening at a second longitudinal edge of the test element 110, e.g., the second side dose position 164. The side dose positions may be an ideal application position for capillary blood from a finger stick. The test element 110 may comprise the top dose position 184 and further may comprise a through hole extending through a cover foil, e.g., the first electrode carrier layer 122, into the capillary 160. The top dose position 184 may be an ideal application position for dosing the sample with a transfer device, e.g., a pipette.

The first electrode contact zone 138 and the second electrode contact zone 146 may be configured to be electrically contacted from opposing sides of the test element 110. The first electrode contact zone 138 may protrude of the layer setup of the test element 110. A punched hole through the cover foil and the spacer layer 134 may be configured as the second electrode contact zone 146, in particular a contact hole 186. In a particular embodiment, two contact holes are punched through the cover foil and the spacer layer 134. Alternatively in a continuous production process, one contact hole is punched at the position where the test elements are individualized in a subsequent cutting process (cutting line) resulting in test elements comprising two lateral contact zones on opposing edges of the final test element. Embodiments with two contact holes or contact zones for each electrode are advantageous if 4-wire-technique is used. The contact hole 186 may have a rectangular shape. FIGS. 5A and 5B show the second electrode being contacted by the connector 178, such as a pair of connectors 178, through the contact hole 186. Thus, the measurement device 172 may comprise one pair of connectors 178 configured to contact the first electrode 116, in this embodiment shown in FIGS. 5A and 5B, from a first direction by the first electrode contact zone 138 and to contact the second electrode 118 from a second direction on the opposite side of the test element 110 through the contact hole 186.

Figure 6:
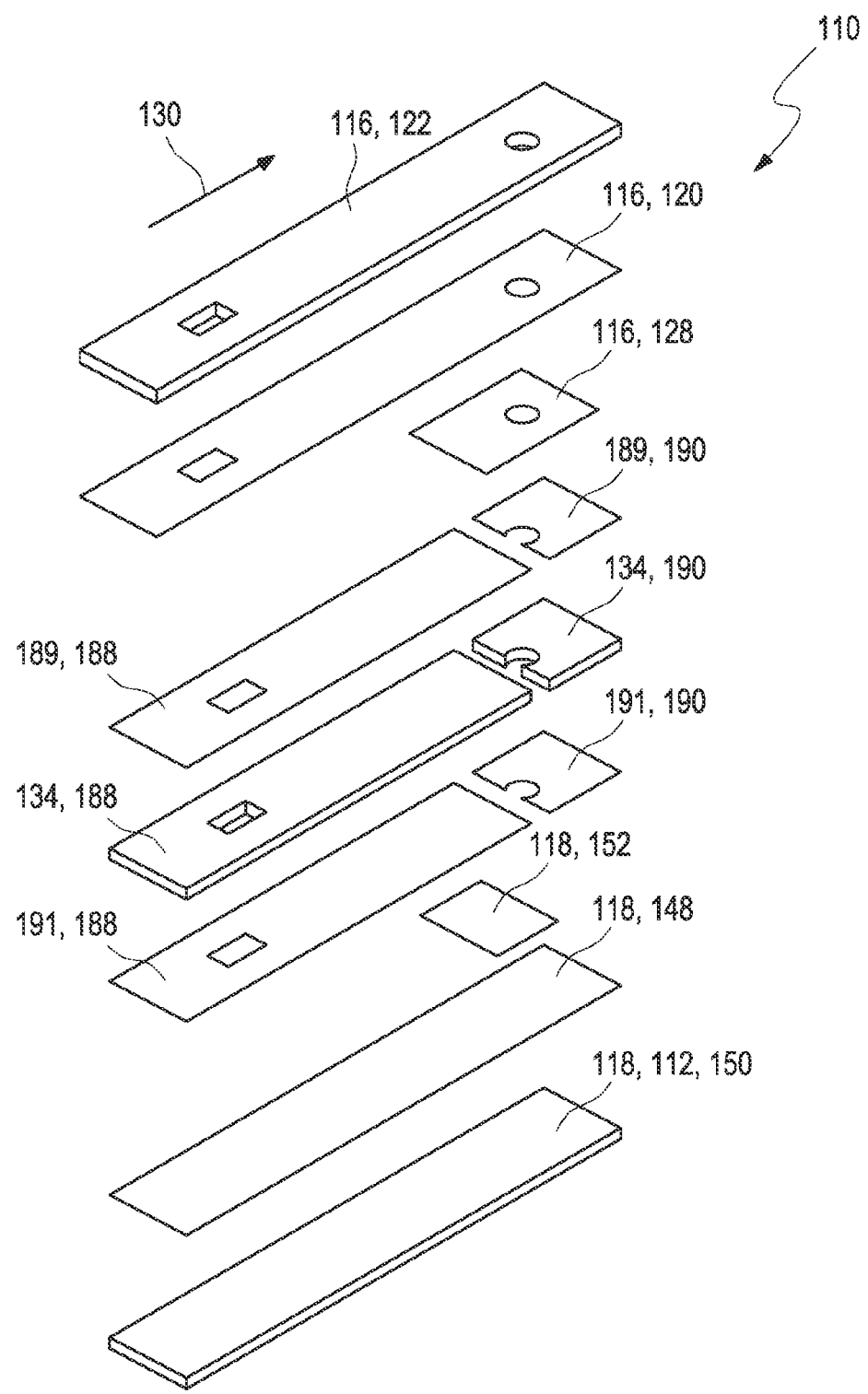
FIG. 6 shows an exploded drawing of the second embodiment of the test element.
Figure 7:
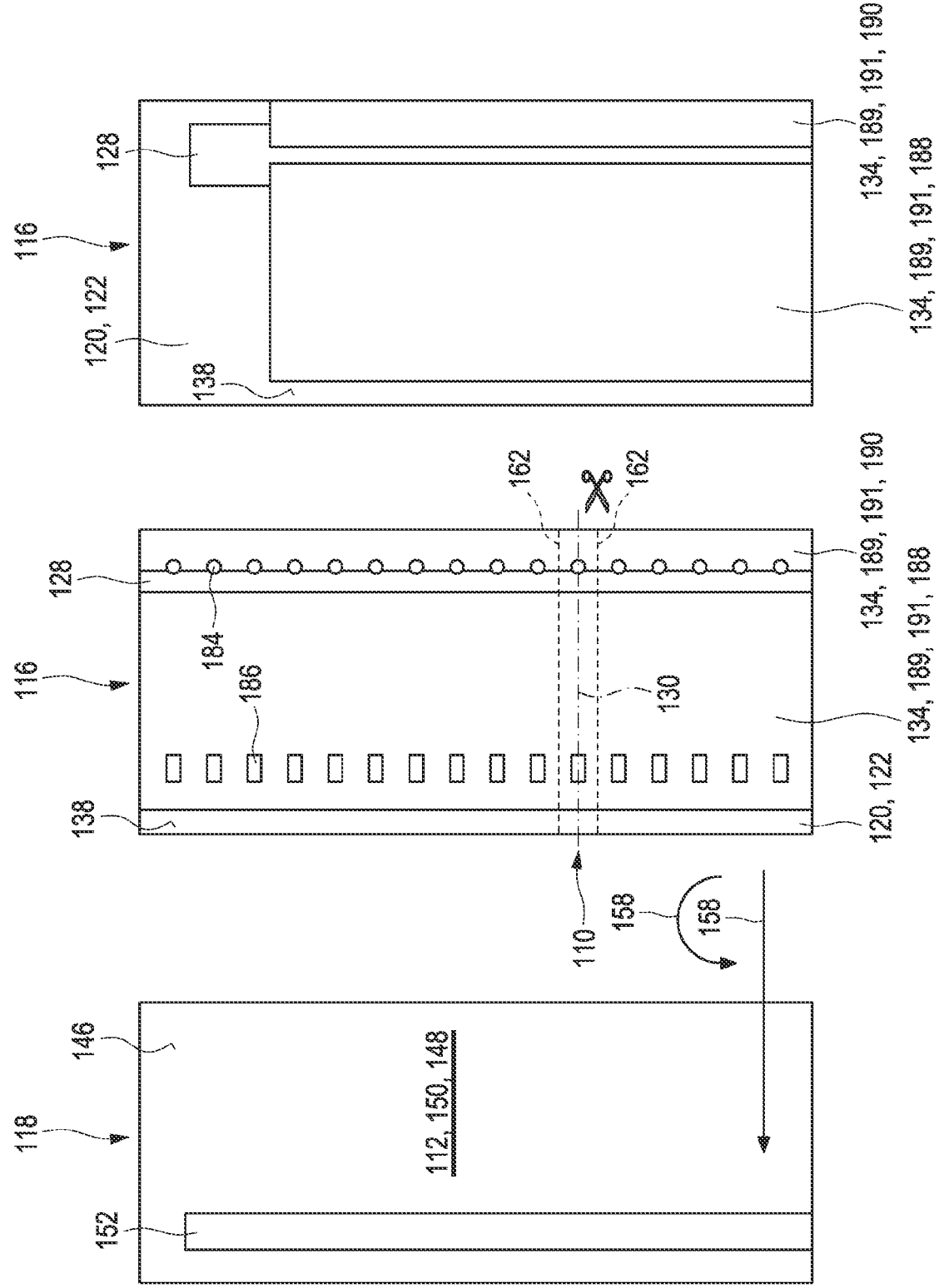
FIG. 7 shows layers of the test element according to the second embodiment in different manufacturing steps.

The contact hole 186 and the top dose position 184 may be realized by punched holes through the cover foil and the spacer layer 134, before a lamination step of the test element 110, typically in one punching step. These holes, the contact hole 186 and the top dose position 184, may be used to trigger a cutting such that the width of an individual test element 110 may be defined by a distance of the punched holes along the cover foil and such that the holes may be positioned in a middle of the width of each test element 110. For this embodiment, no additional turnover element 176 may be required. FIG. 6 shows an exploded drawing of the second embodiment of the test element 110. Regarding the design, structure and production of the first electrode 116 and the second electrode 118, reference can be made to the description of the first embodiment of the test element 110. The spacer layer 134 may be designed comprising at least two portions. The term "in at least two portions" refers to that embodiments, wherein the spacer layer 134 may be designed comprising more than two portions may be feasible, too. Onto the first electrode 116 a first portion 188 of the spacer layer 134 covered with an adhesive layer 189, 191 on both sides may be laminated, such that a channel may be created at the position of the reagent coating 128. A width of the first portion 188 of the spacer layer 134 may be configured such that the first electrode 116 may be partially uncovered, forming the first electrode contact zone 138. Further, onto the first electrode 116 a second portion 190 may be laminated, such that a width and position of the channel between the spacer layer 134 and the first electrode 116 is defined, wherein a width of the second portion 190 may be smaller than a width of the first portion 188. The right column of FIG. 7 shows a laminated layer setup of the first electrode 116 and spacer layer 134.

Further, in a punching step, the holes, the contact hole 186 and the top dose position 184, may be punched through the laminated layer setup of the first electrode 116 and spacer layer 134 by a punching device, typically within one punching step. The punching step may be performed in a continuous process such as a reel-to-reel process. The spacer layer 134 may be covered by a release liner. The top dose position 184 may be arranged such that the punched hole may touch the capillary 160 at one edge. The contact hole 186 may be arranged at an opposing edge of the test element 110. After the punching step, the release liner may be removed from the spacer layer 134. The middle column of FIG. 7 shows the laminated layer setup of the first electrode 116 and spacer layer 134 after the punching step. In a further lamination step, the laminated layer setup of the first electrode 116 and spacer layer 134 may be turned onto the second electrode 118 and may be laminated with the second electrode 118. Arrows 158 shown in FIG. 7 indicate that the depicted laminated second electrode 118 may be turned onto the conductive adhesive 144. The second electrode carrier layer 150 may be configured as the cover foil of the test element 110. The second electrode carrier layer 150 may be coated on one side with the second electrode conductive layer 148, e.g., the second electrode carrier layer 150 may be sputtered with a silver layer. At the position of the capillary 160 an Ag/AgCl paste stripe may be arranged. The laminated second electrode is depicted in the left column of FIG. 7. Finally, the layer setup may be cut into individual test elements 110 such as test strips. The cutting and cutting lines 162 are indicated in FIG. 7.

Figure 8:
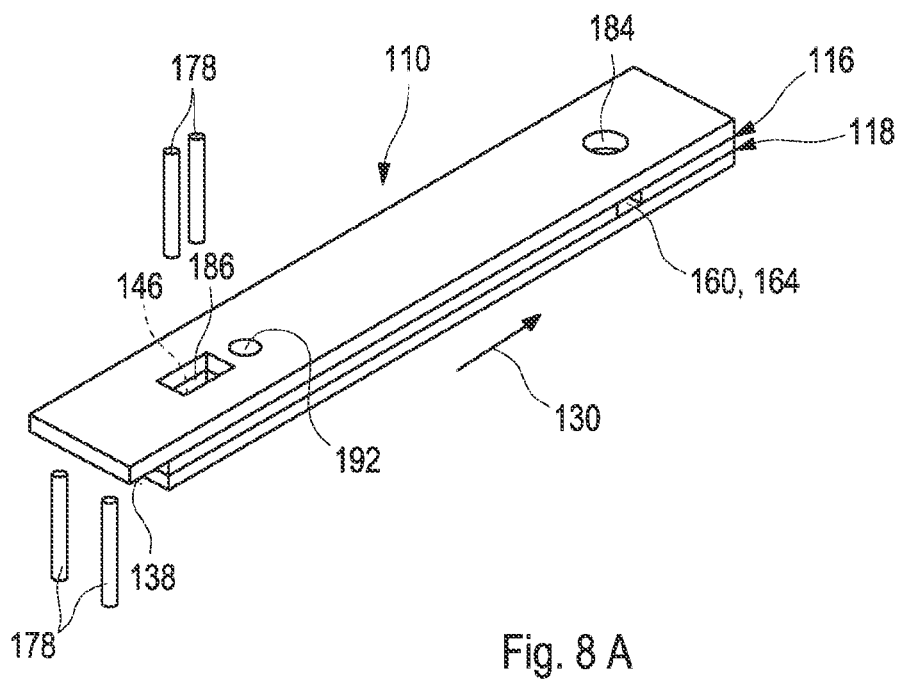
FIG. 8A shows a third embodiment of a test element according to the present disclosure.
FIG. 8B shows the third embodiment of the test element.
FIG. 8C shows a cross-section of the third embodiment of the test element.
Figure 8:
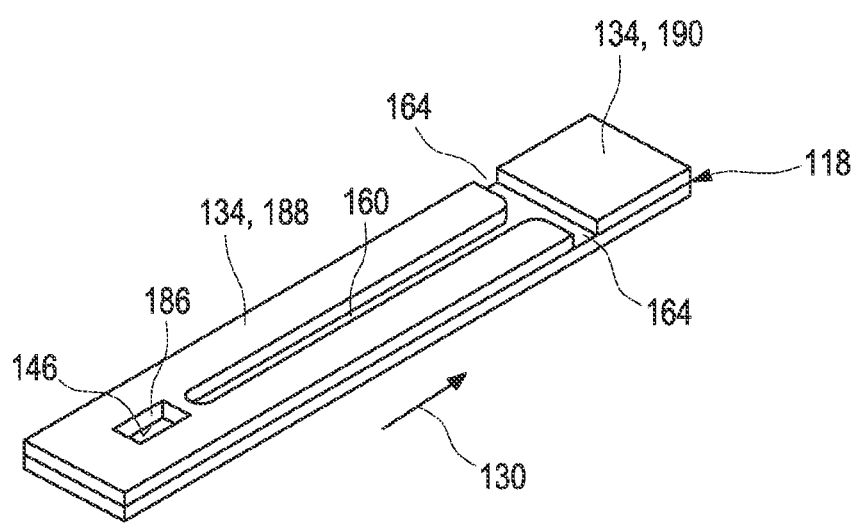
Figure 8C:
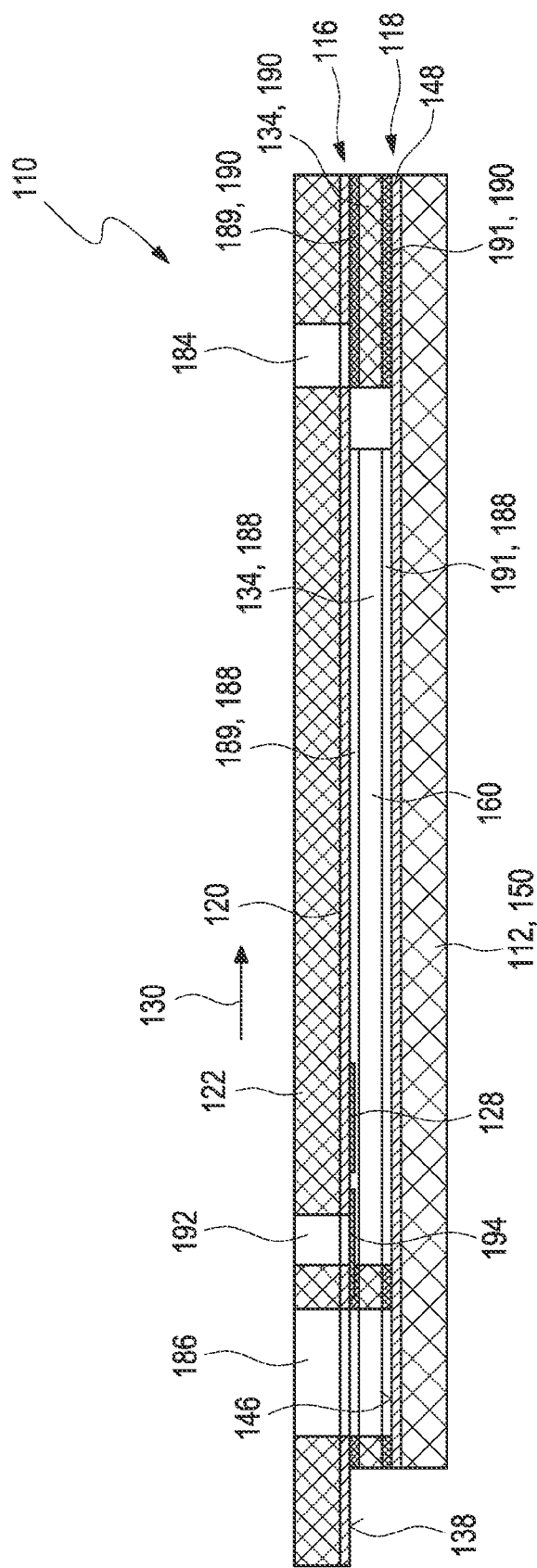

A third embodiment of the test element 110 is shown in FIGS. 8A to 10. For a detailed description of the layer setup of the test element 110, reference can be made to the description of the first and second embodiment above or a description of further embodiments given below. As in the second embodiment, the first electrode 116 and the second electrode 118 may be contacted from opposing sides of the test element 110, e.g., by connectors 178 of the measurement device 172. In the third embodiment of the test element 110, the capillary 160 may at least partially extend along the longitudinal axis 130 of the test element 110, depicted e.g., in FIG. 8B. The forming of the capillary 160 may comprise cutting out the capillary 160 from the spacer layer 134. Thus, the spacer layer 134 may be covered on both sides by an adhesive laminated by a release liner. The cutting may comprise a kiss-cut process. In the cutting process, a cutting profile wheel may be used. The spacer layer 134 may run through a gap between two contrary rotating wheels, wherein one of the wheels may be a kiss-cut wheel with a repeated outlined shape of the capillary 160 at a perimeter. By running through the rotating wheels, the outlined capillary shape may be cut into the spacer layer 134 down to a surface of the opposing release liner. FIG. 8B shows the capillary 160 cut out of the spacer layer 134 laminated on the second electrode 118, whereas FIG. 8C shows a cross section of the test element 110.

Figure 9:
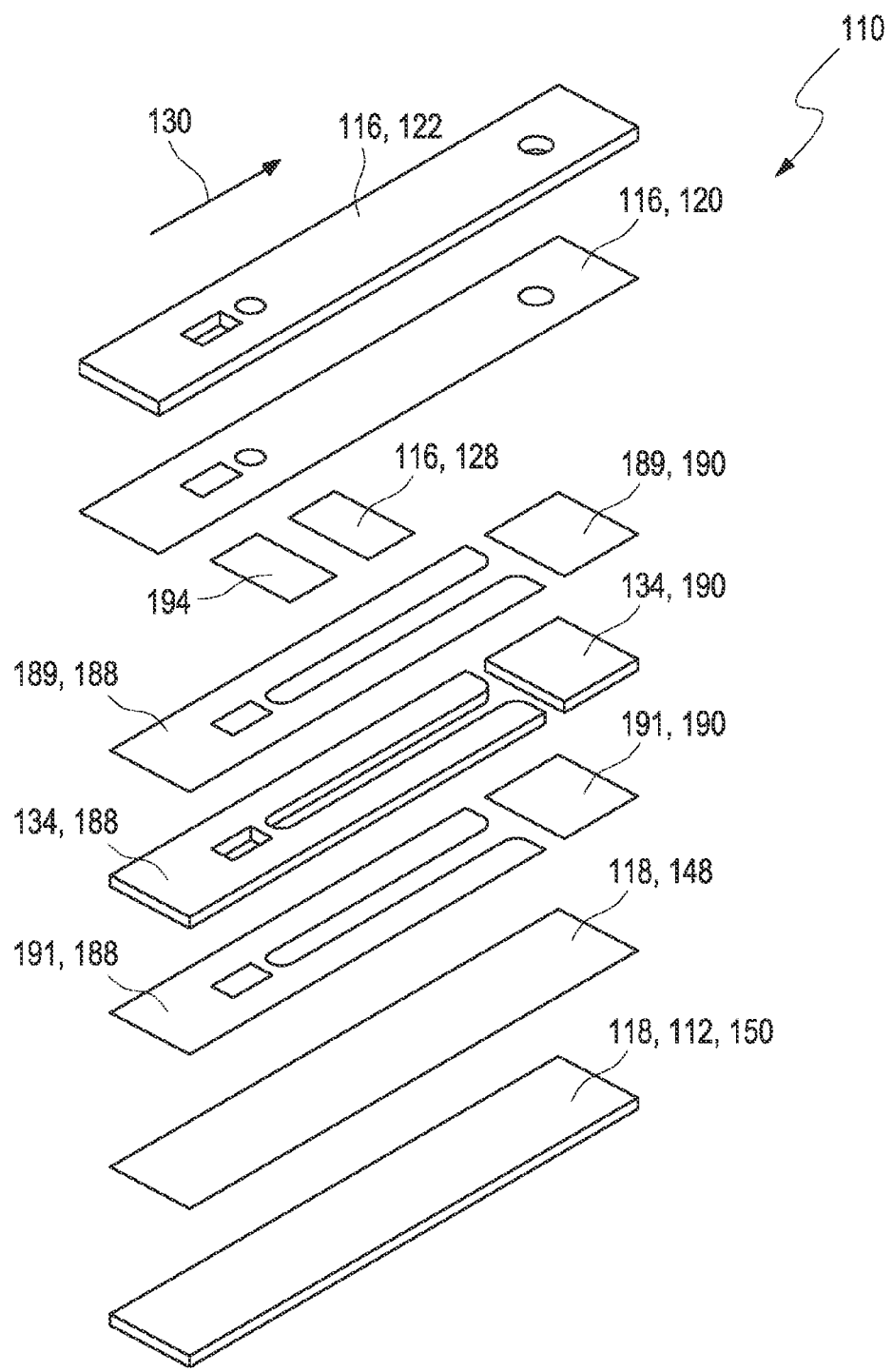
FIG. 9 shows an exploded drawing of the third embodiment of the test element.

The first electrode carrier layer 122 may be coated with a carbon paste or sputtered with a noble metal layer. The reagent coating 128, e.g., the reagent strip, may be arranged close to the measurement device 172, in particular close to a heating device of the measurement device. Thus, it may be possible to heat the sample of body fluid above an ambient temperature, allowing coagulation status parameters to be tested in whole blood samples. The position of the reagent coating 128 may define the measurement zone of the test element 110. The test element 110 may further comprise a vent hole opening 192. Adjacent to the reagent coating, in the direction of the first electrode contact zone 138, the first electrode 116 may be coated by a second reagent, such that a hydrophobic surface 194 following the measurement zone may be created. Hence, the sample of body fluid may be hindered to pass an end of the capillary 160 up to the vent hole 192, such that the measurement device 172 may be contaminated. However, other parts of the surface of the first electrode 116 may be hydrophilic, such that a quick sample transport is ensured. Therefore, the surface may be treated with a detergent. FIG. 9 shows an exploded drawing of the test element 110.

Figure 10:
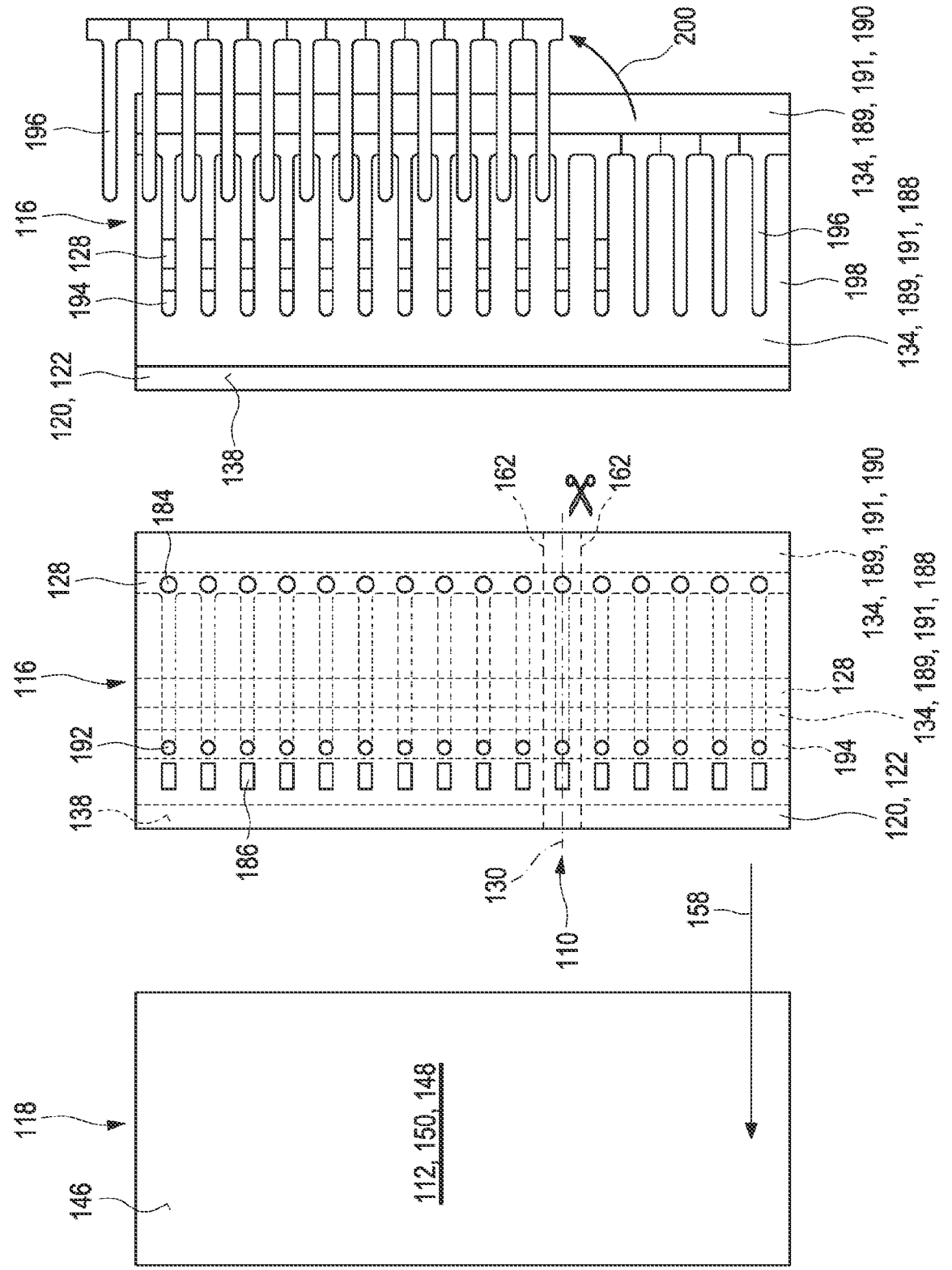
FIG. 10 shows layers of the test element according to the third embodiment in different manufacturing steps.

After the kiss-cut process, one of the release liners may be removed from the spacer layer 134 and the spacer layer 134 may be laminated to the first electrode 116. The spacer layer 134 may be covered with adhesive layers 189, 191 on both sides. Then cut out inner parts 196 of the capillary structure may be pulled off such that outer parts 198 of the capillary structure remain on the first electrode 116. This removing step is depicted on the right column of FIG. 10, e.g., the pulling off is indicated by arrow 200. The structure of the capillary may be used to align the vent hole 192, the top dose position 184, and the second contact hole 186. In a further lamination step, the laminated layer setup of the first electrode 116 and spacer layer 134, shown in the middle column of FIG. 10, may be turned onto the second electrode 118 and may be laminated with the second electrode 118, indicated by arrow 158 shown in FIG. 10. The laminated second electrode is depicted in the left column of FIG. 7. Finally, the layer setup may be cut into individual test elements 110 such as test strips. The cutting and cutting lines 162 are indicated in FIG. 10.

Figure 11:
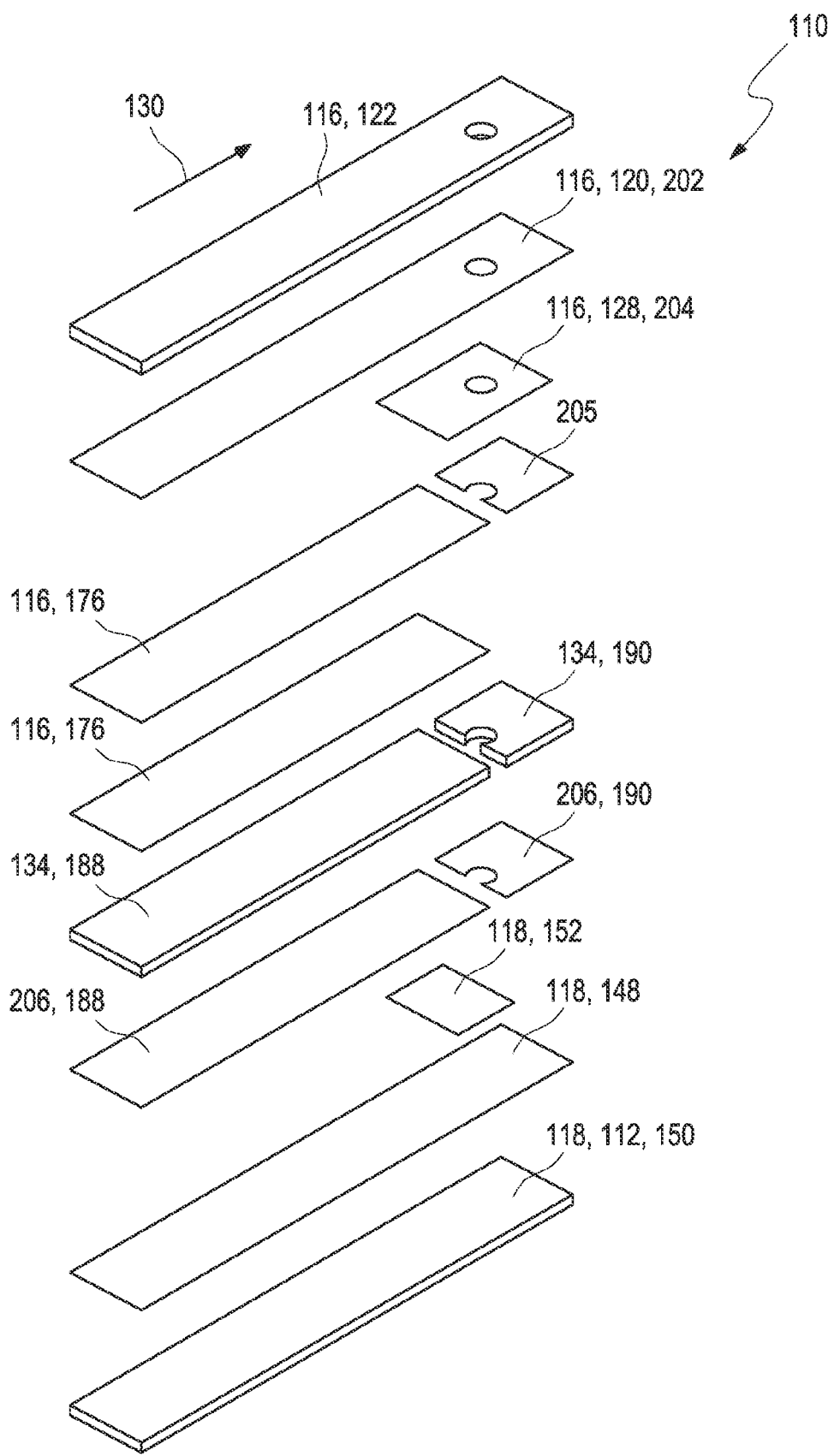
FIG. 11 shows an exploded drawing of an embodiment of the test element according to the present disclosure.

FIG. 11 shows an exploded drawing of an embodiment of the test element 110. In this embodiment, the first electrode carrier layer 122 may be covered by a sputtered aluminum layer 202. The usage of an aluminum layer may be advantageous because of lower raw material costs and better electrical conductivity than carbon pastes or inks. However, the aluminum layer cannot be used directly as electrode material for supporting a redox reaction, because of an oxide layer on a surface of the aluminum layer. The aluminum layer 202 may be combined with a conductive carbon paste. Thus, onto the aluminum layer 202 at a position of the electrochemical cell, a stripe of carbon 204 may be coated. The reagent coating 128 may be coated on top of the carbon stripe 204. An adhesive layer 205 may be arranged between the carbon stripe 204 and the spacer layer 134. The turnover element 176 may be arranged on top of the spacer layer 134, e.g., the turnover element 176 may be designed as a conductive adhesive and a conductive carbon coating. Another side of the spacer layer 134 may be coated with an adhesive layer 206. Alternatively, active ingredients of the detection reagent of the reagent coating 128 may be mixed with the carbon paste and may be coated directly on the aluminum surface. In another embodiment, a conductive carbon transfer adhesive foil may be used, which may be coated homogenously with the reagent coating 128 and may be laminated onto the aluminum layer 202. The usage of carbon on aluminum may be feasible for all described embodiments. In embodiments, wherein the test element 110 may be configured without a protruding carrier element 112 as strip handle 132, a usage of carbon on aluminum may be feasible, too. In these embodiments, the carrier element 112 may be coated with aluminum with a coated carbon stripe and a reagent coating at the position of the electrochemical cell.

Figure 12:
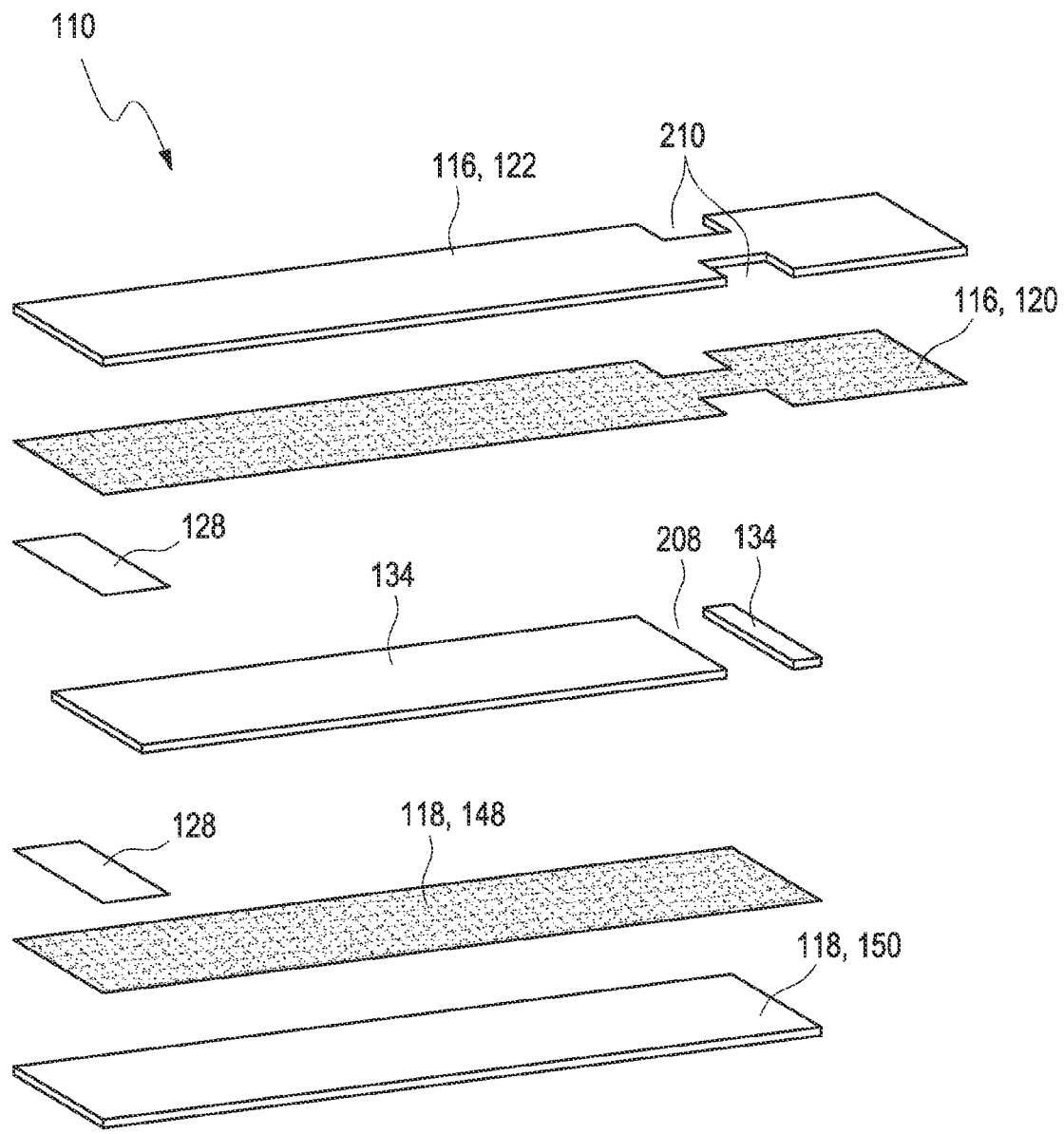
FIG. 12 shows an exploded drawing of an embodiment of the test element according to the present disclosure.
Figure 13:
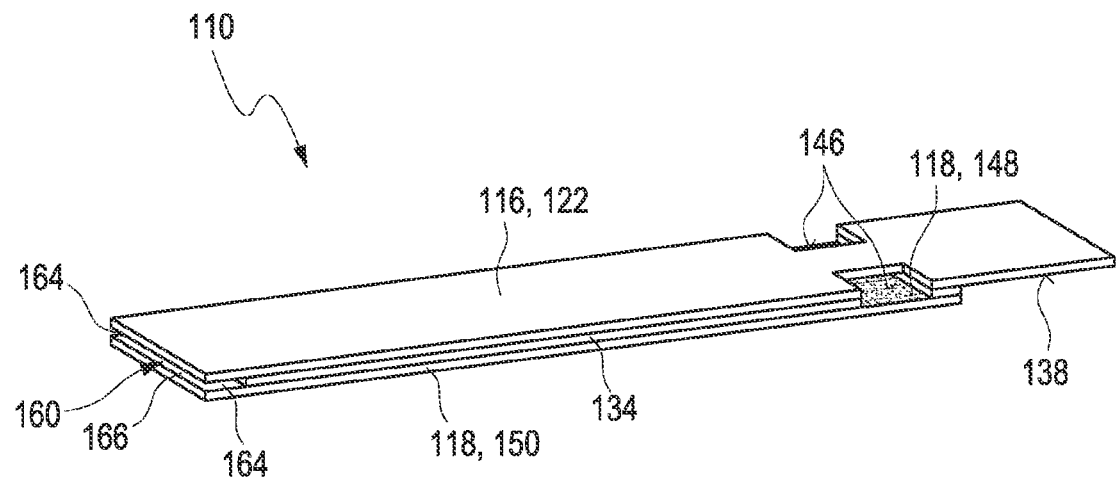
FIG. 13A shows a top view and a bottom view of the embodiment of the test element of FIG. 12.
FIG. 13B shows a top view and a bottom view of the embodiment of the test element of FIG. 12.
Figure 13:
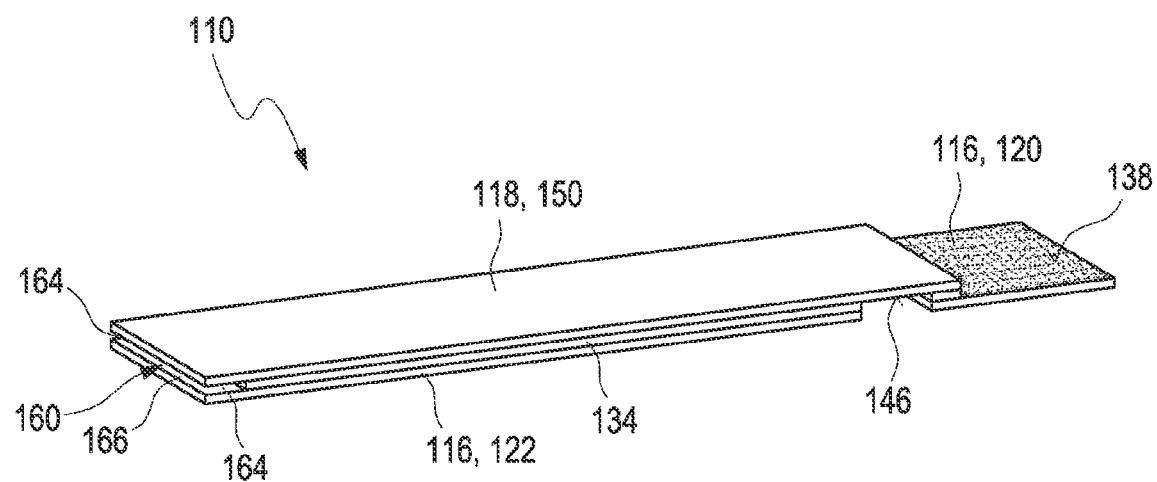

FIG. 12 shows an exploded drawing of an embodiment of the test element 110 according to the present disclosure. FIGS. 13A and 13B show a top view and a bottom view of this embodiment. The test element 110 may comprise a layer setup. The first electrode 116, which is designed as working electrode, may comprise at least one first electrode conductive layer 120. The first electrode conductive layer 120 may comprise a carbon ink coating. The first electrode conductive layer 120 may be disposed on at least one first electrode carrier layer 122. The first electrode carrier layer 122 may be a foil, e.g., a top foil. The first electrode 116 may comprise at least one reagent coating 128, e.g., a detection reagent coating, in contact with the first electrode conductive layer 120. The reagent coating 128 may cover at least partially the first electrode conductive layer 120. The reagent layer 128 may extend over the whole width and length of the capillary 160.

The second electrode 118, which may be designed as counter electrode, may comprise at least one second electrode conductive layer 148. The second electrode conductive layer 148 may comprise a carbon ink coating. The second electrode conductive layer 148 may be disposed on at least one second electrode carrier layer 150. The second electrode carrier layer 150 may be a foil, e.g., a bottom foil. The counter electrode may comprise at least one reagent coating 128 in contact with the second electrode conductive layer 148. The reagent coating 128 may comprise a redox chemistry. The reagent coating may comprise an Ag/AgCl ink. The reagent coating 128 may cover at least partially the second electrode conductive layer 148. The reagent layer 128 may extend over the whole width and length of the capillary 160. The reagent coatings of the first electrode 116 and the second electrode 118 may cover equal areas of the respective electrode conductive layers 120, 148.

At least one spacer layer 134 may be disposed in between the first electrode conductive layer 120 and the second electrode conductive layer 148. The first electrode 116 and the second electrode 118 and the capillary 160 in between the first electrode 116 and the second electrode 118 form an electrochemical cell. The electrochemical cell may extend over the full length of the capillary 160. The first electrode 116 and the second electrode 118 may extend over the full length of the capillary 160. The spacer layer 134 may be arranged such that it does not extend over the full length of the test element 110. For example, the spacer layer 134 may cover the capillary 160 partly. The capillary 160 may be open at three sides. The sample of bodily fluid may be applicable to a side dose position 164 and a front dose position 166, which can be seen best in FIGS. 13A and 13B.

Further, the test element 110 may comprise a first electrode contact zone 138 and a second electrode contact zone 146 configured to contact the first electrode 116 and the second electrode 118 with a further device, e.g., to a measurement device 172. The first electrode contact zone 138 and/or the second electrode contact zone 146 and the side dose position 164 and front dose position 166 may be arranged at opposing ends of the test element 110. The first electrode contact zone 138 and the second electrode contact zone 146 may be arranged in different layers of the layer setup of the test element 110. The first electrode contact zone 138 and the second electrode contact zone 146 may be configured to be electrically contacted from opposing sides of the test element 110.

The first electrode conductive layer 120 and the first electrode carrier layer 122 may form an overhang on the contact side of the test element 110 over the second electrode conductive layer 148 and the second electrode carrier layer 150. Thus, parts of the first electrode conductive layer 120 may be exposed and may allow contacting the first electrode 116 with the further device.

As described above, the spacer layer 134 may be designed such that it does not extend over the full length of the test element 110. The spacer layer 134 may comprise at least one hole and/or at least one recess, which may have an arbitrary form, for example circular or rectangular. The spacer layer 134 may be formed in one part or in multiple parts. The spacer layer 134 may be formed in two parts, wherein the two parts may be aligned with a gap 208 in between. The second electrode contact zone 146 may be formed in the following way: The first electrode conductive layer 120 and the first electrode carrier layer 122 may comprise at least one hole and/or at least one recess, which may have an arbitrary form, for example circular or rectangular. For example, recesses in the first electrode conductive layer 120 and the first electrode carrier layer 122 may be formed by cutting and/or punching. In this embodiment, two rectangular recesses 210 may be present in the first electrode conductive layer 120 and the first electrode carrier layer 122. The spacer layer 134 may be arranged such that, within the layer setup of the test element 110, the spacer layer 134 may not cover recesses 210. Thus, parts of the second electrode conductive layer 148 may be exposed and may allow contacting the second electrode 118 with the further device, e.g., measurement device 172.

LIST OF REFERENCE NUMBERS 110 test element
112 carrier element
114 adhesive layer
116 first electrode 118 second electrode
120 first electrode conductive layer
122 first electrode carrier layer
124 first longitudinal edge
126 second longitudinal edge
128 reagent coating
130 longitudinal axis
132 strip handle
134 spacer layer
136 adhesive layer
138 first electrode contact zone
140 measurement zone
142 conductive material layer
144 conductive adhesive layer
146 second electrode contact zone
148 second electrode conductive layer
150 second electrode carrier layer
151 conductive adhesive layer
152 strip of Ag/AgCl paste
154 first longitudinal edge
156 second longitudinal edge
158 arrows
160 capillary
161 gap
162 cutting lines
164 side dose position
166 front dose position
168 front face
170 system
172 measurement device
174 side
176 turnover element
178 connector
180 arrows
182 arrow
184 top dose position
186 contact hole
188 first portion
189 adhesive layer
190 second portion
191 adhesive layer
192 vent hole opening
194 hydrophobic surface
196 inner parts
198 outer parts
200 Arrow
202 aluminum layer
204 stripe of carbon
205 adhesive layer
206 adhesive layer
208 gap
210 recess It is noted that terms like "preferably", "commonly", and "typically" are not utilized herein to limit the scope of the claimed subject matter or to imply that certain features are critical, essential, or even important to the structure or function of the embodiments disclosed herein. Rather, these terms are merely intended to highlight alternative or additional features that may or may not be utilized in a particular embodiment of the present disclosure.

It is noted that the terms "substantially" and "about" are utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

It will be apparent to those skilled in the art that various modifications and variations can be made to the embodiments described herein without departing from the spirit and scope of the claimed subject matter. Thus, it is intended that the specification cover the modifications and variations of the various embodiments described herein provided such modifications and variations come within the scope of the appended claims and their equivalents.

What is claimed is:

1. A system for determining at least one property of a sample, the system comprising at least one test element, wherein the test element comprises at least one first electrode and at least one second electrode, wherein the first electrode is designed as a working electrode and the second electrode is designed as a counter electrode, wherein the test element comprises at least one capillary capable of receiving a sample of the body fluid, wherein the capillary is open at three sides, wherein a sample of body fluid is applicable to a side dose position and/or a front dose position, wherein the first electrode and the second electrode are arranged on opposing sides of the capillary, wherein the first electrode and the second electrode and the capillary in between the first electrode and the second electrode form an electrochemical cell, wherein the test element is configured to detect the at least one analyte independently of a filling level of the electrochemical cell, wherein the first electrode and the second electrode are arranged such that during a capillary filling the first electrode and the second electrode are wetted simultaneously and at an equal rate, the system further comprising at least one measurement device adapted for performing at least one electrical measurement using the test element, wherein the measurement device is configured to detect both an AC signal and a DC signal simultaneously, wherein both the AC signal and the DC signal are proportional to the filling level of the capillary such that effects due to a filling level of the capillary are compensated, wherein the measurement device is further configured to form a ratio of the AC signal and the DC signal, wherein the ratio is independent from the filling level of the electrochemical cell, wherein the measurement device is configured to detect the at least one analyte independently of a filling level of the electrochemical cell, and wherein the measurement device is configured to apply an AC signal between the at least one first electrode and the at least one second electrode of the test element.

2. The system according to claim 1, wherein the measurement device is further configured to electrically monitor a filling process of the capillary.

3. The system according to claim 1, wherein the measurement device is configured to perform at least one initial failsafe measurement before applying the sample of bodily fluid.

4. A method for determining at least one property of a sample, wherein a system according to claim 1 is used, wherein the method comprises the following steps:
   a) connecting the test element to at least one measurement device;
   b) applying a sample of bodily fluid to a capillary of at least one test element;
   c) determining both an AC signal and a DC signal with said measurement device; and
   d) calibrating measurement results by using the AC and DC signal; and e) determining a filling level of the capillary, wherein an AC signal is applied between the at least one first electrode and the at least one second electrode of the test element.

5. The method according to claim 4, wherein the determination of the AC and DC signal is performed by overlapping excitation potentials.

6. The method according to claim 4, wherein the method further comprises determining a contact time, wherein an AC signal is applied between at least one first electrode and at least one second electrode of the test element, wherein a response over time is measured, and wherein the response is compared to a predefined threshold.

7. The method according to claim 4, wherein a response signal over time is measured, wherein the response is compared to at least one predefined threshold, and wherein the predetermined threshold is chosen such that a minimum filling level is ensured.

8. The method according to claim 7, wherein the predefined threshold is chosen with respect to a specific conductivity of a sample.

9. The method according to claim 4, wherein the method further comprises monitoring a filling process of the capillary, wherein a DC voltage is applied between the first electrode and the second electrode, wherein a DC response is detected, and wherein the DC response is compared to a predefined limit.

10. The system according to claim 1, wherein the first electrode extends over a full length of the capillary, wherein the second electrode extends over the full length of the capillary, and wherein the first electrode and the second electrode are aligned in parallel.

11. A test element for electrochemically detecting at least one analyte in a bodily fluid, wherein the test element comprises at least one first electrode and at least one second electrode, wherein the first electrode is designed as a working electrode and the second electrode is designed as a counter electrode, wherein the test element comprises at least one capillary capable of receiving a sample of the body fluid, wherein the first electrode and the second electrode are arranged on opposing sides of the capillary, wherein the first electrode and the second electrode and the capillary in between the first electrode and the second electrode form an electrochemical cell, wherein the test element is configured to detect the at least one analyte independently of a filling level of the electrochemical cell, wherein the first electrode and the second electrode are arranged such that during a capillary filling the first electrode and the second electrode are wetted simultaneously and at an equal rate, wherein the first electrode extends over a full length of the capillary, wherein the second electrode extends over the full length of the capillary, wherein the first electrode and the second electrode are aligned in parallel, wherein the capillary is open at three sides, wherein a sample of bodily fluid is applicable to one or both of a side dose position or a front dose position, wherein the test element comprises a first electrode contact zone and a second electrode contact zone configured to contact the first electrode and the second electrode with a further device, wherein the first electrode contact zone and the second electrode contact zone are arranged in different layers of a layer setup of the test element, wherein one of the first electrode contact zone and the second electrode contact zone protrudes over the other one of the first electrode contact zone and the second electrode contact zone, wherein the first electrode contact zone and the second electrode contact zone are configured to be electrically contacted from opposing sides of the test element, wherein the test element comprises a layer setup, wherein the first electrode comprises at least one first electrode conductive layer disposed on at least one first electrode carrier layer, wherein the second electrode comprises at least one second electrode conductive layer disposed on at least one second electrode carrier layer, and wherein at least one spacer layer is disposed in between the first electrode conductive layer and the second electrode conductive layer, wherein said further device comprises at least one measurement device adapted for performing at least one electrical measurement using the test element, wherein the measurement device is configured to detect both an AC signal and a DC signal simultaneously, wherein the measurement device is further configured to form a ratio of the AC signal and the DC signal, wherein the ratio is independent from the filling level of the electrochemical cell, and wherein the measurement device is configured to apply an AC signal between the at least one first electrode and the at least one second electrode of the test element.

12. The test element according to claim 11, wherein the test element has an elongated shape extending along a longitudinal axis, wherein the capillary at least partially extends perpendicular to the longitudinal axis, and wherein the capillary extends from a first opening at a first longitudinal edge of the test element to a second opening at a second longitudinal edge of the test element.

* * * * *